(12) United States Patent
Lubisch et al.

(10) Patent No.: US 8,129,389 B2
(45) Date of Patent: *Mar. 6, 2012

(54) SUBSTITUTED OXINDOLE DERIVATIVES, MEDICAMENTS CONTAINING THE LATTER AND USE THEREOF

(75) Inventors: Wilfried Lubisch, Heidelberg (DE); Thorsten Oost, Ludwigshafen (DE); Wolfgang Wernet, Ludwigshafen (DE); Wilfried Hornberger, Ludwigshafen (DE); Liliane Unger, Ludwigshafen (DE); Hervé Geneste, Ludwigshafen (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 494 days.

This patent is subject to a terminal disclaimer.

(21) Appl. No.: 11/886,729

(22) PCT Filed: Mar. 23, 2006

(86) PCT No.: PCT/EP2006/002683
§ 371 (c)(1),
(2), (4) Date: Jan. 13, 2009

(87) PCT Pub. No.: WO2006/100080
PCT Pub. Date: Sep. 28, 2006

(65) Prior Publication Data
US 2009/0186904 A1  Jul. 23, 2009

Related U.S. Application Data

(60) Provisional application No. 60/664,793, filed on Mar. 24, 2005.

(30) Foreign Application Priority Data

Mar. 26, 2005  (DE) .......................... 10 2005 014 936

(51) Int. Cl.
| | |
|---|---|
| A61K 31/496 | (2006.01) |
| A61K 31/506 | (2006.01) |
| C07D 401/12 | (2006.01) |
| C07D 403/12 | (2006.01) |
| C07D 417/12 | (2006.01) |

(52) U.S. Cl. ......... 514/252.11; 514/253.09; 514/252.19; 514/254.02; 514/318; 514/323; 544/364; 544/369; 544/357; 544/293; 544/333; 544/405; 546/194; 546/201

(58) Field of Classification Search .................. None
See application file for complete search history.

(56) References Cited

U.S. PATENT DOCUMENTS

| | | | |
|---|---|---|---|
| 2004/0180878 A1* | 9/2004 | Di Malta et al. | 514/218 |
| 2005/0070718 A1* | 3/2005 | Lubisch et al. | 548/181 |
| 2009/0005397 A1* | 1/2009 | Lubisch et al. | 514/253.09 |

FOREIGN PATENT DOCUMENTS

| | | |
|---|---|---|
| WO | WO 93/15051 | 8/1993 |
| WO | WO 95/18105 A | 7/1995 |
| WO | WO 98/25901 | 6/1998 |
| WO | WO 98/33815 A | 8/1998 |
| WO | WO 01/10900 A | 2/2001 |
| WO | WO 01/55130 A | 8/2001 |
| WO | WO 01/55134 A | 8/2001 |
| WO | WO 01/64668 | 9/2001 |
| WO | WO 01/98295 A | 12/2001 |
| WO | WO 03/008407 | 1/2003 |
| WO | WO 2004/067561 A | 8/2004 |
| WO | WO 2005/030755 A | 4/2005 |
| WO | WO 2006/005609 A2 | 1/2006 |
| WO | WO 2006/072458 A | 7/2006 |

OTHER PUBLICATIONS

Banker et al. "Modern Pharmaceutics", 3rd Ed. p. 596 (1996).*
Wolff, Manfred E. Burger's Medicinal Chemistry, 5th Ed. Part 1, pp. 975-977 (1995).*
Thibonnier, Exp.OPin.Invest.Drugs, vol. 7(5), p. 729-740 (1998).*
Hays, New England Journal of Medicine, vol. 355(20), p. 2146-2148 (2006).*

* cited by examiner

*Primary Examiner* — Emily Bernhardt
(74) *Attorney, Agent, or Firm* — Lisa V. Mueller; Michael Best & Friedrich LLP

(57) ABSTRACT

The invention relates to novel oxindole derivatives of general formula (I), in which the substituents A, B, $R^1$, $R^2$ and $R^3$ are defined as cited in claim 1, to medicaments containing said derivatives and to the use of the latter for the prophylaxis and/or treatment of vasopressin-dependent and/or oxytocin-dependent diseases.

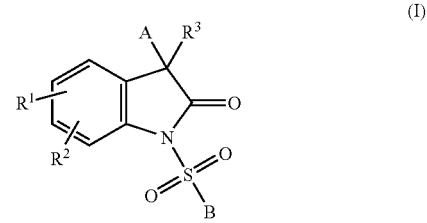

10 Claims, No Drawings

SUBSTITUTED OXINDOLE DERIVATIVES, MEDICAMENTS CONTAINING THE LATTER AND USE THEREOF

The present invention relates to novel oxindole derivatives and to medicaments comprising them for the treatment of diseases.

Vasopressin (AVP) is an endogenous hormone which exerts various effects on organs and tissues. Vasopressin is related to oxytocin (OT), so that the two peptides are combined to form a vasopressin/oxytocin family. It is suspected that the vasopressin/oxytocin system is involved in various pathological states such as, for example, heart failure and high blood pressure. At present, three vasopressin receptors (V1a, V1b or V3 and V2 receptors) and one oxytocin receptor (OT receptor), via which vasopressin and oxytocin mediate their effects, are known. Antagonists of these receptors, especially including antagonists which bind specifically only to one of the above receptors, represent novel therapeutic approaches to the treatment of diseases. (M. Thibonnier, Exp. Opin. Invest. Drugs 1998, 7(5), 729-740). It has been found, for example, that a selective antagonist of the vasopressin V1b receptor exerts anxiolytic and antidepressant effects in animal models (Griebel et al., PNAS 2002, 99, 6370; Serradeil-Le Gal et al., J. Pharm. Exp. Ther. 2002, 300, 1122). Since the models described have a certain predictive value for the clinical effects to be expected, antagonists of the V1b receptor are of particular interest for the treatment of emotional disturbances or disorders such as, for example, stress, anxiety states and/or depression.

Oxytocin is a hormone which is produced in neurosecretory neurons of the hypothalamus and—bound to neurophysins—is transported to the posterior pituitary lobe and is stored there. Oxytocin stimulates contraction of the uterine muscles and of the myoepithelial cells of the mammary gland (ejection of milk); the contractility of the uterus is altered by estrogens (promoting effect) and progestogens (inhibiting effect). Oxytocin is broken down by the enzyme oxytocinase. Oxytocin is used in obstetrics (e.g. for the induction of labor, in the event of postpartum uterine atony) (quoted from: Roche Lexikon Medizin 5th edition).

The present application describes novel substituted oxindoles which have an arylsulfonyl group in position 1. 1-Phenylsulfonyl-1,3-dihydro-2H-indol-2-ones have previously been described as ligands of vasopressin receptors. WO 93/15051, WO95/18105, WO 98/25901, WO 01/55130, WO 01/55134, WO 01/164668 and WO 1/98295 have described derivatives derived from the oxindole structure and having arylsulfonyl groups in position 1. These compounds differ essentially in the substitution in position 3.

In particular, WO 93/15051 and WO 98/25901 describe 1-phenylsulfonyl-1,3-dihydro-2H-indol-2-ones, in which the oxindole structure is substituted in position 3 by two alkyl radicals which may likewise be a cycloalkyl radical (spiro linkage), as ligands of vasopressin receptors. As alternative, the spiro ring may comprise heteroatoms such as oxygen and nitrogen (optionally with substituents).

WO 95/18105 describes 1-phenylsulfonyl-1,3-dihydro-2H-indol-2-ones which have a nitrogen atom in position 3 as ligands of vasopressin receptors. In addition, radicals which may be alkyl, cycloalkyl, phenyl or benzyl radicals are bonded in position 3 (in each case optionally with substituents).

Other publications, for example WO 01/55130, describe compounds which have nitrogen-containing rings (e.g. proline, homoproline, morpholine, tetrahydroisoquinoline, dihydroindole; in each case optionally with substituents) which are linked via their nitrogen atom to position 3 of the oxindole structure but which are substituted by phenylsulfonyl or phenyl groups (optionally with substituents) both in position 1 and in position 3 on the oxindole ring.

WO 03/008407 describes 1-phenylsulfonyloxindoles in which pyridylpiperazines are linked via an oxycarbonyl group to the oxindole in position 3.

It is an object of the present invention to provide novel compounds for the treatment or prophylaxis of various vasopressin-dependent or oxytocin-dependent diseases. The compounds should have a high and selective activity for one of the receptors from the vasopressin/oxytocin receptor family, especially the V1b receptor. It was further intended that the compounds show improvements compared with known compounds, especially higher selectivity in relation to binding to the V1a and OT receptors, better metabolic stability and better pharmacological activity in suitable models which enable prognostic statements to be made about use in therapy.

The object is achieved by compounds of the general formula (I)

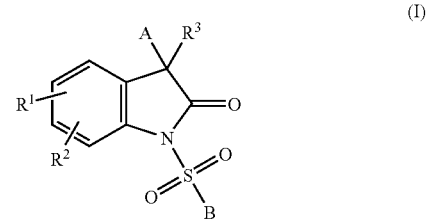

in which

A can be phenyl or naphthalene, each of which can be substituted by one, two, three or four radicals $R^4$ which are selected independently of one another from the group consisting of hydrogen, chlorine, bromine, iodine, fluorine, $(CH_2)_{0-2}$—CN, $CF_3$, $OCF_3$, $CONH_2$, $CONH(C_1-C_4\text{-alkyl})$, $CON(C_1-C_4\text{-alkyl})(C_1-C_4\text{-alkyl})$, NHCHO, $NHCONH_2$, $NH(C_0-C_4\text{-alkylene})CONH_2$, $NH(C_0-C_4\text{-alkylene})CONH(C_1-C_4\text{-alkyl})$, $NHCOCH_3$, $NO_2$, $(CH_2)_{0-2}$—OH, O—$C_1-C_6$-alkyl, $(CH_2)_{1-2}$—O—$C_1-C_4$-alkyl, O—$C_0-C_4$-alkylene-phenyl, phenyl, $C_1-C_6$-alkyl, $C_2-C_6$-alkenyl and $C_2-C_6$-alkynyl, B is an aromatic or partially aromatic monocyclic or bicyclic system which may be composed of 6, 7, 8, 9 or 10 C atom members and which may be substituted by one, two, three or four radicals selected from the group consisting of the radicals $R^6$, $R^7$, $R^8$ and $R^9$, where $R^6$, $R^7$, $R^8$ and $R^9$ are selected, independently of one another and independently of their respective occurrence, from the group consisting of hydrogen, chlorine, bromine, iodine, fluorine, $(CH_2)_{0-2}$—CN, $CF_3$, $OCF_3$, $CONH_2$, $CONH(C_1-C_4\text{-alkyl})$, $CON(C_1-C_4\text{-alkyl})(C_1-C_4\text{-alkyl})$, NHCHO, $NH(C_{0-4}\text{-alkylene})CONH(C_1-C_4\text{-alkyl})$, $NHCOCH_3$, $NO_2$, OH, O—$C_1-C_4$-alkyl, $(CH_2)_{0-2}$—O—$(CH_2)_{0-3}$—$CH_3$, O—$C_0-C_4$-alkylene-phenyl, phenyl, $C_1-C_6$-alkyl, $C_2-C_6$-alkenyl and $C_2-C_6$-alkynyl;

$R^1$ is CN;

$R^2$ is hydrogen, $C_1-C_4$-alkyl, O—($C_1-C_4$-alkyl), Cl or F;

$R^3$ is a radical (W)—(X)—(Y)—Z, where

W is $C_1-C_4$-alkylene, $(C_0-C_4\text{-alkylene})$-O—$(C_0-C_4\text{-alkylene})$ or $(C_0-C_4\text{-alkylene})$-$NR^5$—$(C_0-C_4\text{-alkylene})$, in which $R^5$ is hydrogen or $C_1-C_4$-alkyl, X is CO, $SO_2$, (C=NH) or (C=N—CN);

Y is a radical selected from the group consisting of the radicals

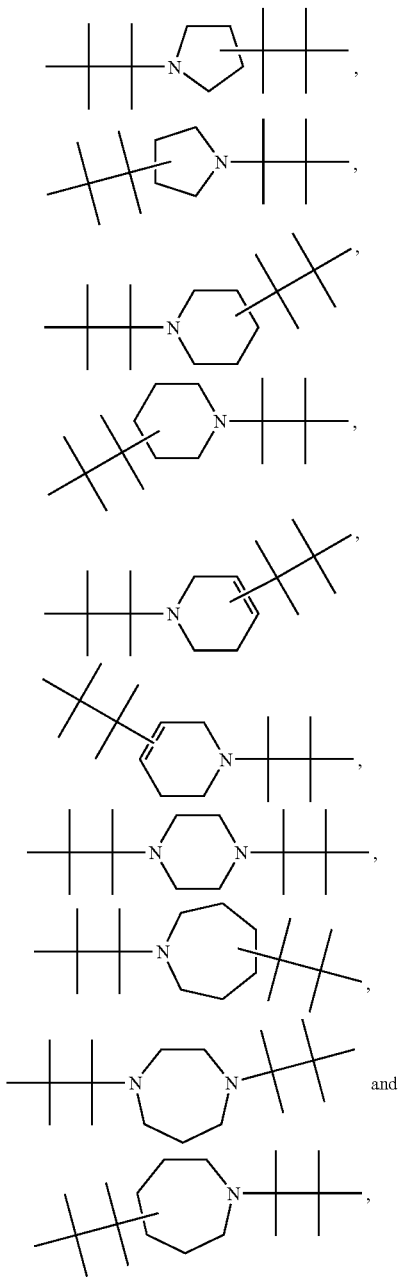

and and where Y may additionally be substituted by the radicals $R^{10}$ and $R^{11}$, where $R^{10}$ and $R^{11}$ may have independently of one another the following meanings, namely $R^{10}$ may be hydrogen, $C_1$-$C_6$-alkyl, $C_2$-$C_6$-alkenyl, $C_2$-$C_6$-alkynyl, OH, O—$C_1$-$C_4$-alkyl, O—$C_0$-$C_4$-alkylene-phenyl, $NH_2$, $NH(C_1$-$C_4$-alkyl) or $N(C_1$-$C_4$-alkyl)($C_1$-$C_4$-alkyl), $R^{11}$ may be hydrogen, $C_1$-$C_6$-alkyl, $C_2$-$C_6$-alkenyl, $C_2$-$C_6$-alkynyl, OH, O—$C_1$-$C_4$-alkyl, O—$C_0$-$C_4$-alkylene-phenyl, $NH_2$, $NH(C_1$-$C_4$-alkyl) or $N(C_1$-$C_4$-alkyl)($C_1$-$C_4$-alkyl), and Z is a mono-, bi- or tricyclic heteroaromatic ring system which may consist of 5, 6, 7, 8, 9, 10, 11, 12, 13, 14 or 15 ring members, where the ring members may, besides C atoms, also be one, two, three, four, five, six or seven identical or different heteroatoms selected from the group consisting of O, N and S, and the hetero ring members may be present in one, two or distributed in the rings, where the ring system can comprise not more than one S ring member, two O ring members and 4 N ring members, and where the ring system comprises at least one heteroatom selected from the group consisting of S, O and N as ring member and where Z may additionally be substituted by the radicals $R^{12}$, $R^{13}$ and $R^{14}$, where $R^{12}$, $R^{13}$ and $R^{14}$ may have independently of one another the meanings mentioned below, namely $R^{12}$ may be hydrogen, chlorine, bromine, iodine, fluorine, $(CH_2)_{0-2}$—CN, $CF_3$, $OCF_3$, $CONH_2$, COOH, $CONH(C_1$-$C_4$-alkyl), $CON(C_1$-$C_4$-alkyl)($C_1$-$C_4$-alkyl), NHCHO, $NHCONH_2$, $N(C_0$-$C_4$-alkylene)$CONH_2$, $NH(C_0$-$C_4$-alkylene)$CONH(C_1$-$C_4$-alkyl), $NHCOCH_3$, $NO_2$, $(CH_2)_{0-2}$—OH, O—$C_1$-$C_6$-alkyl, $(CH_2)_{0-2}$—O—$C_1$-$C_4$-alkyl, O—$C_0$-$C_4$-alkylene-phenyl, phenyl, $C_1$-$C_6$-alkyl, $C_2$-$C_6$-alkenyl and $C_2$-$C_6$-alkynyl, $NH_2$, $NH(C_1$-$C_4$-alkyl) or $N(C_1$-$C_4$-alkyl)($C_1$-$C_4$-alkyl);

$R^{13}$ may be hydrogen, chlorine, bromine, iodine, fluorine, $(CH_2)_{0-2}$—CN, $CF_3$, $OCF_3$, $CONH_2$, COOH, $CONH(C_1$-$C_4$-alkyl), $CON(C_1$-$C_4$-alkyl)($C_1$-$C_4$-alkyl), NHCHO, $NHCONH_2$, $N(C_0$-$C_4$-alkylene)$CONH_2$, $NH(C_0$-$C_4$-alkylene)$CONH(C_1$-$C_4$-alkyl), $NHCOCH_3$, $NO_2$, $(CH_2)_{0-2}$—OH, O—$C_1$-$C_6$-alkyl, $(CH_2)_{0-2}$—O—$C_1$-$C_4$-alkyl, O—$C_0$-$C_4$-alkylene-phenyl, phenyl, $C_1$-$C_6$-alkyl, $C_2$-$C_6$-alkenyl and $C_2$-$C_6$-alkynyl, $NH_2$, $NH(C_1$-$C_4$-alkyl) or $N(C_1$-$C_4$-alkyl)($C_1$-$C_4$-alkyl);

$R^{14}$ may be hydrogen, chlorine, fluorine, $C_1$-$C_6$-alkyl, $C_2$-$C_6$-alkenyl, $C_2$-$C_6$-alkynyl or $C_0$-$C_4$-alkylene-phenyl;

and their tautomeric, enantiomeric and/or diastereomeric forms, and their prodrugs, and the physiologically tolerated salts of said compounds.

A preferred embodiment of the invention relates to compounds of the general formula (I), in which $R^1$, $R^2$ and $R^3$ may have the abovementioned meanings and the variables A and B independently of one another have the following meanings:

A is a phenyl ring which may be substituted by one or two radicals $R^4$, where $R^4$ may independently of one another have the abovementioned meanings;

B is a phenyl ring which may be substituted by one, two, three or four radicals selected from the group consisting of the radicals $R^6$, $R^7$, $R^8$ and $R^9$, where $R^6$, $R^7$, $R^8$ and $R^9$ may independently of one another and independently of their respective occurrence have the abovementioned meanings;

and the tautomeric, enantiomeric and/or diastereomeric forms thereof, and prodrugs thereof, and the physiologically tolerated salts of said compounds.

A further preferred embodiment of the invention relates to compounds of the general formula (I), in which the variables independently of one another have the following meanings:

A is a phenyl ring which may be substituted by one or two radicals $R^4$ which are selected independently of one another from the group consisting of hydrogen, chlorine, O—$C_1$-$C_4$-alkyl, $(CH_2)_{1-2}$—O—$(CH_2)_{0-2}$—$CH_3$ and $C_1$-$C_6$-alkyl, B is a phenyl ring which may be substituted by one, two, three or four radicals selected from the group consisting of the radicals $R^6$, $R^7$, $R^8$ and $R^9$, where $R^6$, $R^7$, $R^8$ and $R^9$ are selected independently of one another and independently of their respective occurrence from the group consisting of hydrogen, fluorine, chlorine, CN, $NO_2$, O—$C_1$-$C_4$-alkyl, $(CH_2)_{1-2}$—O—$(CH_2)_{0-2}$—$CH_3$ and $C_1$-$C_6$-alkyl, $R^1$ is CN and is located in position 5 of the oxindole of the formula (I), $R^2$ is hydrogen, $R^3$ is a radical (W)—(X)—(Y)—Z, where
W is O, CH$_2$NH, NHCH$_2$, OCH$_2$, CH$_2$O or NH,
X is CO, (C=NH) or (C=N—CN),
Y is a radical selected from the group consisting of the respective radicals

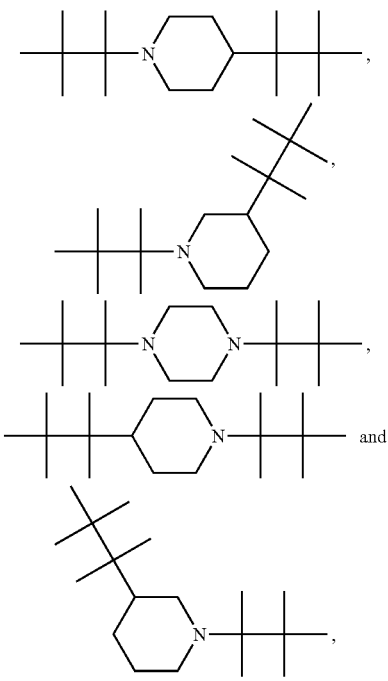

and

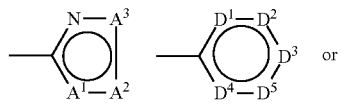

Z is a radical selected from the group consisting of the radicals

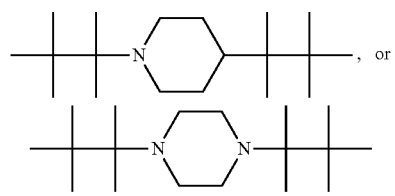 or

Z is a radical selected from the group consisting of the radicals benzimidazolyl, benzofuranyl, benzothiazolyl, benzoxazolyl, indolyl, 5-azaindolyl, 6-azaindolyl, 7-azaindolyl, imidazo[1,5-a]pyridinyl and pyrazolo[1,5-a]pyridinyl, where
A$^2$ and A$^3$ may independently of one another be N or C;
A$^1$ may be N, C, O or S;
D$^1$, D$^2$, D$^3$, D$^4$ and D$^5$ may independently of one another be C or N, but where at least one of the variables D$^1$, D$^2$, D$^3$, D$^4$ or D$^5$ is N,
and where
Z may in each case additionally be substituted by the radicals R$^{12}$, R$^{13}$ and R$^{14}$, where R$^{12}$, R$^{13}$ and R$^{14}$ may independently of one another have the meanings stated below, namely
R$^{12}$ may be hydrogen, chlorine, fluorine, CN, CF$_3$, OCF$_3$, CONH$_2$, NHCONH$_2$, NHCOCH$_3$, NO$_2$, OH, O—C$_1$-C$_4$-alkyl, C$_1$-C$_6$-alkyl, NH$_2$, NH(C$_1$-C$_4$-alkyl) or N(C$_1$-C$_4$-alkyl)(C$_1$-C$_4$-alkyl);
R$^{13}$ may be hydrogen, fluorine, chlorine, CN, CF$_3$, OCF$_3$, CONH$_2$, NHCONH$_2$, NHCOCH$_3$, NO$_2$, OH, O—C$_1$-C$_4$-alkyl, C$_1$-C$_6$-alkyl, NH$_2$, NH(C$_1$-C$_4$-alkyl) or N(C$_1$-C$_4$-alkyl)(C$_1$-C$_4$-alkyl);
R$^{14}$ may be hydrogen, fluorine, chlorine or C$_1$-C$_4$-alkyl;
and the tautomeric, enantiomeric and/or diastereomeric forms thereof, and prodrugs thereof, and the physiologically tolerated salts of said compounds.

A further preferred embodiment of the invention relates to compounds of the general formula (I), in which the variables independently of one another have the following meanings:
A is a phenyl ring which may be substituted by one radical R$^4$, where R$^4$ may be chlorine, O—C$_1$-C$_4$-alkyl, or C$_1$-C$_6$-alkyl;
B is a phenyl ring which may be substituted by one or two radicals selected from the group consisting of the radicals R$^6$ and R$^7$, where R$^6$ and R$^7$ are independently of one another and independently of their respective occurrence selected from the group consisting of hydrogen, fluorine, chlorine, CN, NO$_2$, O—C$_1$-C$_4$-alkyl and C$_1$-C$_6$-alkyl;
R$^1$ is CN and is located in position 5 of the oxindole of the formula (I);
R$^2$ is hydrogen;
R$^3$ is a radical (W)—(X)—(Y)—Z, where
W is O, CH$_2$ or NH,
X is CO, (C=NH) or (C=N—CN),
Y is a radical selected from the respective radicals

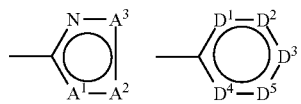, or

Z is a radical selected from the group consisting of the radicals

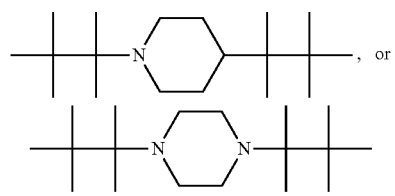

where
A$^2$ and A$^3$ may independently of one another be N or C;
A$^1$ may be N, C, O or S;
D$^1$, D$^2$, D$^3$, D$^4$ and D$^5$ may independently of one another be C or N, but where at least one of the variables D$^1$, D$^2$, D$^3$, D$^4$ and D$^5$ is N,
and where
Z may in each case be substituted by the radicals R$^{12}$, R$^{13}$ and R$^{14}$, where R$^{12}$, R$^{13}$ and R$^{14}$ may independently of one another have the meanings stated below, namely
R$^{12}$ may be hydrogen, chlorine, fluorine, CN, CF$_3$, OCF$_3$, CONH$_2$, NHCOCH$_3$, NO$_2$, OH, OC—C$_1$-C$_4$-alkyl, C$_1$-C$_4$-alkyl, NH$_2$, NH(C$_1$-C$_4$-alkyl) or N(C$_1$-C$_4$-alkyl)(C$_1$-C$_4$-alkyl);
R$^{13}$ may be hydrogen, fluorine, chlorine, OCH$_3$ or C$_1$-C$_4$-alkyl;
R$^{14}$ is hydrogen;
and the tautomeric, enantiomeric and/or diastereomeric forms thereof, and prodrugs thereof, the physiologically tolerated salts of said compounds.

A further preferred embodiment of the invention relates to compounds of the general formula (I), in which the variables independently of one another have the following meanings:
A is a phenyl ring which may be substituted by R$^4$, where R$^4$ may be chlorine, OCH$_2$CH$_3$, OCH(CH$_3$)$_2$, OCH$_2$CH$_2$CH$_3$, CH$_2$CH$_3$, CH(CH$_3$)$_2$, or CH$_2$CH$_2$CH$_3$,
B is a phenyl ring which may be substituted by one or two radicals selected from the group consisting of the radicals R$^6$ and R$^7$, where R$^6$ and R$^7$ are independently of one another and independently of their respective occurrence selected from the group consisting of hydrogen, fluorine, chlorine, CN, $NO_2$, $O-C_1-C_4$-alkyl, and $C_1-C_6$-alkyl;
$R^1$ is CN and is located in position 5 of the oxindole of the formula (I);
$R^2$ is hydrogen;
$R^3$ is a radical (W)—(X)—(Y)—Z, where
W is $CH_2$, O or NH,
X is CO or (C=NH),
Y is the radical

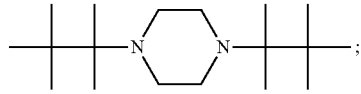

Z is a radical selected from the group consisting of the radicals pyridinyl, pyrimidinyl, pyrazinyl, thiazolyl, isoxazolyl, imidazolyl and phthalazinyl
and where
Z may in each case be substituted by $R^{12}$ and $R^{13}$, where $R^{12}$ and $R^{13}$ may independently of one another have the meanings stated below, namely
$R^{12}$ may be hydrogen, chlorine, fluorine, CN, $CF_3$, $OCF_3$, OH, $OC_1-C_4$-alkyl, $C_1-C_4$-alkyl, $NH_2$, $NH(C_1-C_4$-alkyl) or $N(C_1-C_4$-alkyl)($C_1-C_4$-alkyl);
$R^{13}$ may be hydrogen, fluorine or $C_1-C_4$-alkyl;
and the tautomeric, enantiomeric and/or diastereomeric forms thereof, and prodrugs thereof, and the physiologically tolerated salts of said compounds.

A further preferred embodiment of the invention relates to compounds of the general formula (I), in which the variables independently of one another have the following meanings:
A is a phenyl ring which is substituted by $O-CH_2CH_3$ in ortho position,
B is a phenyl ring which is substituted by one or two radicals selected from the group consisting of the radicals $R^6$ and $R^7$, where $R^6$ and $R^7$ are selected independently of one another and independently of their respective occurrence from the group consisting of hydrogen, fluorine, chlorine, CN, $NO_2$, $O-C_1-C_4$-alkyl, and $C_1-C_6$-alkyl,
$R^1$ is CN and is located in position 5 of the oxindole of the formula (I),
$R^2$ is hydrogen,
$R^3$ is a radical (W)—(X)—(Y)—Z, where
W is $CH_2$, O or NH,
X is CO or (C=NH),
Y is a radical

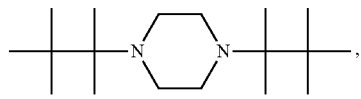

Z is a radical selected from the group consisting of the radicals and where Z may in each case be substituted by the radicals $R^{12}$ and $R^{13}$,

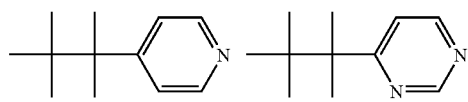

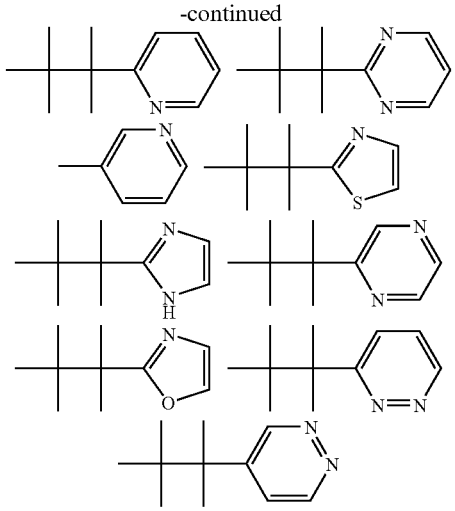

where $R^{12}$ and $R^{13}$ may independently of one another have the meanings stated below, namely
$R^{12}$ may be hydrogen, chlorine, fluorine, CN, $CF_3$, $OCF_3$, OH, $OCH_3$, $CH_3$, $CH_2CH_3$, $CH(CH_3)_2$, $NH_2$, $NHCH_3$ or $N(CH_3)_2$;
$R^{13}$ may be hydrogen, chlorine, fluorine or $CH_3$, $CH_2CH_3$;
and the tautomeric, enantiomeric and/or diastereomeric forms thereof, and prodrugs thereof, and the physiologically tolerated salts of said compounds.

The variables which characterize the inventive compounds of the formula (I) have independently of one another the following preferred meanings.

A is preferably a phenyl ring which may be substituted by a maximum of four radicals $R^4$, more preferably a phenyl ring which may be substituted by a maximum of two radicals $R^4$. If A is substituted, the substituents $R^4$ are selected independently of one another from the group consisting of hydrogen, chlorine, bromine, iodine, fluorine, $(CH_2)_{0-2}$—CN, $CF_3$, $OCF_3$, $CONH_2$, $CONH(C_1-C_4$-alkyl), $CON(C_1-C_4$-alkyl)($C_1-C_4$-alkyl), NHCHO, $NHCONH_2$, $NH(C_0-C_4$-alkylene)$CONH_2$, $NH(C_0-C_4$-alkylene)$CONH(C_1-C_4$-alkyl), $NHCOCH_3$, $NO_2$, $(CH_2)_{0-2}$—OH, $O-C_1-C_6$-alkyl, $(CH_2)_{1-2}$—$O-C_1-C_4$-alkyl, $O-CO-C_4$-alkylene-phenyl, phenyl, $C_1-C_6$-alkyl, $C_2-C_6$-alkenyl and $C_2-C_6$-alkynyl, preferably hydrogen, chlorine, $O-C_1-C_4$-alkyl, $(CH_2)_{1-2}$—O—$(CH_2)_{0-2}$—$CH_3$ and $C_1-C_6$-alkyl, more preferably hydrogen, chlorine, $O-C_1-C_4$-alkyl and $C_1-C_4$-alkyl. If A is a phenyl ring, one substituent is preferably located in position 2, and further substituents may be in positions 3, 4 or 5, more preferably one substituent is located in position 2 and a further one in position 3, 4 or 5, and most preferably one substituent is located in position 2.

B is preferably a phenyl ring which may be substituted by the radicals $R^6$, $R^7$, $R^8$ and/or $R^9$, more preferably a phenyl ring which may be substituted by the radicals $R^6$ and/or $R^7$. If B is substituted, the substituents $R^6$, $R^7$, $R^8$ and/or $R^9$ are selected independently of one another from the group consisting of hydrogen, chlorine, bromine, iodine, fluorine, $(CH_2)_{0-2}$—CN, $CF_3$, $OCF_3$, $CONH_2$, $CONH(C_1-C_4$-alkyl), $CON(C_1-C_4$-alkyl)($C_1-C_4$-alkyl), NHCHO, $NH(C_{0-4}$-alkylene)$CONH(C_1-C_4$-alkyl), $NHCOCH_3$, $NO_2$, OH, $O-C_1-C_4$-alkyl, $(CH_2)_{1-2}$—O—$(CH_2)_{0-3}$—$CH_3$, $O-C_0-C_4$-alkylene-phenyl, phenyl, $C_1-C_6$-alkyl, $C_2-C_6$-alkenyl and $C_2-C_6$-alkynyl, preferably hydrogen, fluorine, chlorine, $O-C_1-C_4$-alkyl, $(CH_2)_{1-2}$—O—$(CH_2)_{0-2}$—$CH_3$ and $C_1-C_6$-alkyl, more preferably hydrogen, fluorine, chlorine, $O-C_1-C_4$-alkyl and $C_1$-$C_6$-alkyl. If B is a phenyl ring, the substituents are preferably located in position 2, 3, 4, 5 and/or 6, a maximum of 4 substituents is preferred, of which two substituents are in position 2 and position 4, or one substituent is either in position 2 or position 4, more preferably two substituents are in position 2 and position 4 or one substituent is either in position 2 or position 4.

$R^1$ is CN and is preferably located in position 5 of the oxindole of the general formula (I).

$R^2$ is preferably hydrogen.

$R^3$ is a radical (W)—(X)—(Y)—Z, where preferred definitions of $R^3$ are evident from the definitions of W, X, Y and Z, in which at least one of the definitions of W, X, Y and Z represents any preferred embodiment as explained below. All the definitions of W, X, Y and Z preferably represent any preferred embodiment. $R^3$ is most preferably a radical (W)—(X)—(Y)—Z, where all the definitions of W, X, Y and Z represent the most preferred embodiment in each case.

W is preferably O, ($C_1$-$C_4$-alkylene)NH, NH($C_1$-$C_4$-alkylene), O($C_1$-$C_4$-alkylene), ($C_1$-$C_4$-alkylene)O or NH, more preferably O, $CH_2$NH, $NHCH_2$, $OCH_2$, $CH_2O$ or NH, most preferably $CH_2$, O or NH.

X is preferably CO, (C=NH) and (C=N—CN), most preferably CO and (C=NH).

Y is preferably

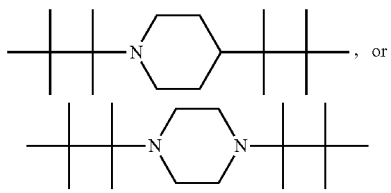, or and most preferably

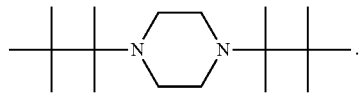.

$R^{10}$ is preferably hydrogen or $C_1$-$C_4$-alkyl, where the alkyl group may be located in position 2, 3, 5 or 6, preferably hydrogen or a $C_1$-$C_4$-alkyl group which is located in position 2, and particularly preferably hydrogen.

$R^{11}$ is preferably hydrogen or $C_1$-$C_4$-alkyl, where the alkyl group may be located in position 2, 3, 5 or 6, preferably hydrogen or a $C_1$-$C_4$-alkyl group which is located in position 2, and particularly preferably hydrogen.

Z is preferably imidazolyl, thiazolyl, oxazolyl, isoxazolyl, 1,2,3-triazolyl, 1,3,4-triazolyl, pyrazolyl, tetrazolyl, thiadiazolyl, thiaoxazolyl, pyridinyl, pyrimidinyl, pyrazinyl, phthalazinyl, 1,3,5-triazinyl, 1,2,4-triazinyl, benzimidazolyl, benzothiazolyl, benzoxazolyl, indolyl, 5-azaindolyl, 6-azaindolyl, 7-azaindolyl, imidazo[1,5-a]pyridinyl, pyrazolo[1,5-a]pyridinyl, and pyridyl, pyrimidinyl, phthalazinyl, pyrazinyl, thiazolyl, isoxazolyl, imidazolyl are particularly preferred.

These heteroaromatic systems with the following substitution are especially preferred

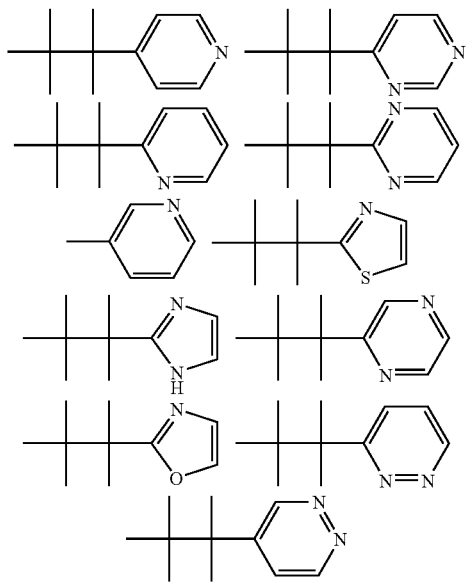

$R^{12}$ is preferably hydrogen, chlorine, fluorine, CN, $CF_3$, $OCF_3$, $CONH_2$, $NHCONH_2$, $NHCOCH_3$, $NO_2$, OH, O—$C_1$-$C_4$-alkyl, $C_1$-$C_6$-alkyl, $NH_2$, NH($C_1$-$C_4$-alkyl) or N($C_1$-$C_4$-alkyl)($C_1$-$C_4$-alkyl), and hydrogen, chlorine, fluorine, CN, $CF_3$, $OCF_3$, OH, $OCH_3$, $CH_3$, $CH_2CH_3$, $CH(CH_3)_2$, $NH_2$, $NHCH_3$ or $N(CH_3)_2$ are particularly preferred $R^{13}$ is preferably hydrogen, chlorine, fluorine, CN, $CF_3$, $OCF_3$, $CONH_2$, $NHCONH_2$, $NHCOCH_3$, $NO_2$, OH, O—$C_1$-$C_4$-alkyl, $C_1$-$C_6$-alkyl, $NH_2$, NH($C_1$-$C_4$-alkyl) or N($C_1$-$C_4$-alkyl)($C_1$-$C_4$-alkyl), and hydrogen, chlorine, fluorine and $CH_3$, $CH_2CH_3$ are particularly preferred.

$R^{14}$ is preferably hydrogen, fluorine, chlorine and $C_1$-$C_4$-alkyl and particularly preferably hydrogen.

A further preferred embodiment of the invention relates to compounds of the general formula (I) having a binding affinity Ki for the vasopressin V1b receptor subtype of less than about 100 nM, preferably not more than 10 nM and in particular not more than 5 nM, e.g. from 0.01 to less than 100 nM or from 0.1 to less than 100 nM or from 1 to less than 100 nM or from 10 to less than 100 nM or from 0.01 to 10 nM or from 0.1 to 10 nM or from 1 to 10 nM or from 1 to nM.

A further preferred embodiment of the invention relates to compounds of the general formula (I), which have a selectivity for the vasopressin V1b receptor subtype vis-à-vis the vasopressin V1a receptor subtype, the quotient of Ki(V1a)/Ki(V1b) being greater than 1.

A further preferred embodiment of the invention relates to compounds of the general formula (I), which have a selectivity for the vasopressin V1b receptor subtype vis-à-vis the vasopressin V2 receptor subtype, the quotient of Ki(V2)/Ki(V1b) being greater than 1.

A further preferred embodiment of the invention relates to compounds of the general formula (I), which have a selectivity for the vasopressin V1b receptor subtype vis-à-vis the oxytocin (OT) receptor, the quotient of Ki(OT)/Ki(V1b) being greater than 1.

A further preferred embodiment of the invention relates to compounds of the general formula (I), which have a binding affinity Ki for the vasopressin V1b receptor subtype of less than 100 nM, preferably not more than 10 nM and in particular not more than 5 nM, e.g. from 0.01 to less than 100 nM or from 0.1 to less than 100 nM or from 1 to less than 100 nM or from 10 to less than 100 nM or from 0.01 to 10 nM or from 0.1 to 10 nM or from 1 to 10 nM or from 1 to 5 nM, and a selectivity for the vasopressin V1b receptor subtype vis-à-vis the vasopressin V1a receptor subtype, that is the quotient of Ki(V1a)/Ki(V1b) is greater than 1.

A further preferred embodiment of the invention relates to compounds of the general formula (I), which have a binding affinity Ki for the vasopressin V1b receptor subtype of less than 100 nM, preferably not more than 10 nM, in particular not more than 5 nM, e.g. from 0.01 to less than 100 nM or from 0.1 to less than 100 nM or from 1 to less than 100 nM or from 10 to less than 100 nM or from 0.01 to 10 nM or from 0.1 to 10 nM or from 1 to 10 nM or from 1 to 5 nM, and a selectivity for the vasopressin V1b receptor subtype vis-à-vis the vasopressin V2 receptor subtype, the quotient of Ki(V2)/Ki(V1b) being greater than 1.

A further preferred embodiment of the invention relates to compounds of the general formula (I), which have a binding affinity Ki for the vasopressin V1b receptor subtype of less than 100 nM, preferably not more than 10 nM, in particular not more than 5 nM, e.g. from 0.01 to less than 100 nM or from 0.1 to less than 100 nM or from 1 to less than 100 nM or from 10 to less than 100 nM or from 0.01 to 10 nM or from 0.1 to 10 nM or from 1 to 10 nM or from 1 to 5 nM, and a selectivity for the vasopressin V1b receptor subtype vis-à-vis the oxytocin (OT) receptor, the quotient of Ki(OT)/Ki(V1b) being greater than 1.

A further preferred embodiment of the invention relates to compounds of the general formula (I), which have a binding affinity Ki for the vasopressin V1b receptor subtype of less than 100 nM, preferably not more than 10 nM, in particular not more than 5 nM, e.g. from 0.01 to less than 100 nM or from 0.1 to less than 100 nM or from 1 to less than 100 nM or from 10 to less than 100 nM or from 0.01 to 10 nM or from 0.1 to 10 nM or from 1 to 10 nM or from 1 to 5 nM, and selectivities for the vasopressin V1b receptor subtype vis-à-vis the vasopressin V1a receptor subtype and the vasopressin V2 receptor subtype, the quotients of Ki(V1a)/Ki(V1b) and Ki(V2)/Ki(V1b) being in each case greater than 1.

A further preferred embodiment of the invention relates to compounds of the general formula (I), which have a binding affinity Ki for the vasopressin V1b receptor subtype of less than 100 nM, preferably not more than 10 nM, in particular not more than 5 nM, e.g. from 0.01 to less than 100 nM or from 0.1 to less than 100 nM or from 1 to less than 100 nM or from 10 to less than 100 nM or from 0.01 to 10 nM or from 0.1 to 10 nM or from 1 to 10 nM or from 1 to 5 nM, and simultaneous selectivities for the vasopressin V1b receptor subtype vis-à-vis the vasopressin V1a receptor subtype and the oxytocin (OT) receptor, the quotients of Ki(V1a)/Ki(V1b) and Ki(OT)/Ki(V1b) being in each case greater than 1.

A further preferred embodiment of the invention relates to compounds of the general formula (I), which have a binding affinity Ki for the vasopressin V1b receptor subtype of less than 100 nM, preferably not more than 10 nM, in particular not more than 5 nM, e.g. from 0.01 to less than 100 nM or from 0.1 to less than 100 nM or from 1 to less than 100 nM or from 10 to less than 100 nM or from 0.01 to 10 nM or from 0.1 to 10 nM or from 1 to 10 nM or from 1 to 5 nM, and simultaneous selectivities for the vasopressin V1b receptor subtype vis-à-vis the vasopressin V2 receptor subtype and the oxytocin (OT) receptor, the quotients of Ki(V2)/Ki(V1b) and Ki(OT)/Ki(V1b) being in each case greater than 1.

A further preferred embodiment of the invention relates to compounds of the general formula (I), which have a binding affinity Ki for the vasopressin V1b receptor subtype of less than 100 nM, preferably not more than 10 nM, in particular not more than 5 nM, e.g. from 0.01 to less than 100 nM or from 0.1 to less than 100 nM or from 1 to less than 100 nM or from 10 to less than 100 nM or from 0.01 to 10 nM or from 0.1 to 10 nM or from 1 to 10 nM or from 1 to 5 nM, and simultaneous selectivities for the vasopressin V1b receptor subtype vis-à-vis the vasopressin V1a receptor subtype, the vasopressin V2 receptor subtype and the oxytocin (OT) receptor, the quotients of Ki(V1a)/Ki(V1b), Ki(V2)/Ki(V1b) and Ki(OT)/Ki(V1b) being in each case greater than 1.

A further aspect of the present invention relates to compounds of the general formula (I) for use as medicament.

A further aspect of the present invention relates to a medicament comprising at least one compound of the general formula (I).

A further aspect of the present invention relates to the use of at least one compound of the general formula (I) for producing a medicament for the treatment and/or prophylaxis of vasopressin-dependent and/or oxytocin-dependent diseases.

A further aspect of the present invention relates to the use of at least one compound of the general formula (I) for producing a medicament for the treatment and/or prophylaxis of at least one disorder selected from the group consisting of diabetes insipidus, nocturnal enuresis, incontinence, diseases in which blood coagulation disorders occur, and for delaying micturition.

A further aspect of the present invention relates to the use of at least one compound of the general formula (I) for producing a medicament for the treatment and/or prophylaxis of at least one disorder selected from the group consisting of hypertension, pulmonary hypertension, heart failure, myocardial infarction, coronary spasm, unstable angina, PTCA (percutaneous transluminal coronary angioplasie), ischemias of the heart, disorders of the renal system, edemas, renal vasospasm, necrosis of the renal cortex, hyponatremia, hypokalemia, Schwartz-Bartter syndrome, disorders of the gastrointestinal tract, gastric vasospasm, hepatocirrhosis, gastric and intestinal ulcer, emesis, emesis occurring during chemotherapy, and travel sickness.

A further aspect of the present invention relates to the use of at least one compound of the general formula (I) for producing a medicament for the treatment and/or prophylaxis of affective disorders.

A further aspect of the present invention relates to the use of at least one compound of the general formula (I) for producing a medicament for the treatment and/or prophylaxis of anxiety disorders and stress-dependent anxiety disorders.

A further aspect of the present invention relates to the use of at least one compound of the general formula (I) for producing a medicament for the treatment and/or prophylaxis of memory impairments and/or Alzheimer's disease.

A further aspect of the present invention relates to the use of at least one compound of the general formula (I) for producing a medicament for the treatment and/or prophylaxis of psychoses and/or psychotic disorders.

A further aspect of the present invention relates to the use of at least one compound of the general formula (I) for producing a medicament for the treatment and/or prophylaxis of Cushing's syndrome.

A further aspect of the present invention relates to the use of at least one compound of the general formula (I) for producing a medicament for the treatment of sleep disorders.

A further aspect of the present invention relates to the use of at least one compound of the general formula (I) for producing a medicament for the treatment and/or prophylaxis of depressive disorders.

A further aspect of the present invention relates to a method for the therapeutic and/or prophylactic treatment of a mammal requiring a treatment by administering an effective amount of at least one compound of the general formula (I) for the treatment of at least one disease as described above.

In a preferred embodiment, the mammal in the method described above is a human, a nonhuman animal or a nonhuman transgenic animal.

A further aspect of the present invention relates to a process for preparing compounds of the general formula (I), wherein the compounds of the general formula (I) can be prepared by process steps known per se and/or with analogous application of process steps known per se to the relevant skilled worker with knowledge of the present invention.

Each of these preferred definitions of one variables can be combined with any definitions of the remaining variables.

The inventive compounds can be in the form of racemates or of enantiopure or diastereopure compounds. The compounds may further be in non-salt form or optionally in salt form with physiologically tolerated acids or bases and may likewise be in the form of prodrugs.

Physiologically tolerated salts can be formed for example with the following anions:
chloride, bromide, phosphate, carbonate, nitrate, perchlorate, sulfate, citrate, lactate, tartrate, maleate, fumarate, mandelate, benzoate, ascorbate, cinnamate, glycollate, methanesulfonate, formate, malonate, naphthalene-2-sulfonate, tosylates, salicylate and/or acetate. Further suitable acids are listed for example in "Fortschritte der Arzneimittelforschung", 1966, Birkhäuser Verlag, vol. 10, pp. 224-285.

The terms "alkyl" or "alkylene" in the meaning of the present description always comprise unbranched or branched "alkyl" or "alkylene".

$C_1$-$C_4$-Alkyl is in the meaning of the description preferably methyl, ethyl, n-propyl, i-propyl, n-butyl, sec-butyl or t-butyl.

$C_0$-Alkylene or $(CH_2)_0$ designate in the meaning of the description a single bond.

$C_1$-$C_4$-Alkylene is in the meaning of the description methylene, ethylene or branched or unbranched propylene or butylene.

$C_1$-$C_6$-Alkyl is in the meaning of the description methyl, ethyl or branched or unbranched propyl, butyl, pentyl or hexyl, preferably $C_1$-$C_4$-alkyl, i.e. methyl, ethyl, n-propyl, i-propyl, n-butyl, sec-butyl or t-butyl.

$C_1$-$C_6$-Alkylene is in the meaning of the description methylene, ethylene or branched or unbranched propylene, butylene, pentylene or hexylene, preferably $C_1$-$C_4$-alkylene, i.e. methylene, ethylene or branched or unbranched propylene or butylene.

The symbol

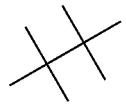

in the chemical formulae of Y and Z indicates the points of linkage of Y with X and Z and the points of linkage of Z with Y. In the formulae of Y, each point of linkage may represent a bond to X or to Z.

The inventive compounds are effective after administration by various routes, especially orally.

The inventive compounds show good affinity for vasopressin receptors, especially the vasopressin V1b receptor subtype. Since the various vasopressin receptors mediate very different effects of vasopressin (M. Thibonnier, Exp. Opin. Invest. Drugs 1998, 7(5), 729-740; Serradeil-Le Gal, C, et al.; Prog Brain Res. 2002; 139:197-210), it is particularly important to obtain effects selectively on, for example, one vasopressin receptor, in order thus to achieve the desired effect without simultaneously causing considerable side effects. Thus, vasopressin mediates for example effects on the kidney and its function via the V2 receptor, and this would be unwanted during a possible treatment of CNS disorders. Accordingly, besides the actual affinity for the target receptor, also particularly important is the selectivity vis-à-vis the other vasopressin receptors. The inventive compounds show the advantage of having very good affinities for the vasopressin V1b receptor and simultaneously displaying an improved selectivity vis-à-vis the other receptors such as V1a, V2 and OT.

The present invention also provides the use of the inventive compounds for the treatment and/or prophylaxis of diseases in which the course of the disease is at least partially dependent on vasopressin, i.e. diseases which show an elevated vasopressin or oxytocin level which may contribute indirectly or indirectly to the pathological state.

The present invention further provides the use of the inventive compounds for the treatment and/or prophylaxis of diseases such as, for example, diabetes insipidus, nocturnal enuresis, incontinence, diseases in which blood coagulation disorders occur and/or for delaying micturition.

The present invention also provides the use of the inventive compounds for the treatment and/or prophylaxis of the following diseases: hypertension, pulmonary hypertension, heart failure, myocardial infarction, coronary spasm, unstable angina, PTCA (percutaneous transluminal coronary angioplasie), ischemias of the heart, disorders of the renal system, edemas, renal vasospasm, necrosis of the renal cortex, hyponatremia, hypokalemia, Schwartz-Bartter syndrome, disorders of the gastrointestinal tract, gastritic vasospasm, hepatocirrhosis, gastric and intestinal ulcer, emesis, emesis occurring during chemotherapy, and travel sickness.

The inventive compounds can also be used for the treatment of various vasopressin-dependent or oxytocin-dependent complaints which have central nervous causes or causes in the HPA axis (hypothalamic pituitary adrenal axis), for example for affective disorders such as depressive disorders and bipolar disorders. These include for example dysthymic disorders, phobias, post-traumatic stress disorders, general anxiety disorders, panic disorders, seasonal depressions and sleep disorders. The disorders which can be treated according to the invention and which are associated with alterations in the HPA axis also include the disorders associated with drug withdrawal, especially withdrawal of opioid drugs or cocaine, including the increased tendency to relapse of formerly dependent individuals.

The inventive compounds can likewise be employed for treatment in cases of anxiety disorders and stress-dependent anxiety disorder such as, for example, generalized anxiety disorders, phobias, post-traumatic anxiety disorders, panic anxiety disorders, obsessive-compulsive anxiety disorders, acute stress-dependent anxiety disorders and social phobia. The inventive compounds can further be employed also for the treatment of memory impairments, Alzheimer's disease, psychoses, psychotic disorders, sleep disorders and/or Cushing's syndrome.

The compounds of the invention are further suitable for the treatment of psychotic disorders/impairments such as schizophrenia.

The compounds of the invention are further suitable for the treatment of vasomotor disorders (vasomotor symptoms VMS) such as hot flushes or night sweats, and thus also for the prophylaxis of the sequalae associated therewith, such as lack of sleep and disorders and impairments resulting therefrom.

The present invention also relates to pharmaceutical compositions which comprise an effective dose of an inventive compound or of a pharmaceutically acceptable salt thereof and suitable pharmaceutical carriers.

These pharmaceutical carriers are chosen according to the pharmaceutical form and the desired mode of administration.

The inventive compounds of the general formula I or optionally suitable salts of these compounds can be used to produce pharmaceutical compositions for oral, sublingual, subcutaneous, intramuscular, intravenous, topical, intratracheal, intranasal, transdermal or rectal administration and be administered to animals or humans in standard administration forms, mixed with conventional pharmaceutical carriers, for the prophylaxis or treatment of the above disorders or diseases.

The suitable standard administration forms comprise forms for oral administration, such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The inventive compounds can be used in creams, ointments or lotions for topical administration.

In order to achieve the desired prophylactic or therapeutic effect, the dose of the active basic ingredient can vary between 0.01 and 50 mg per kg of body weight and per day.

Each unit dose may comprise from 0.05 to 5000 mg, preferably 1 to 1000 mg, of the active ingredient in combination with a pharmaceutical carrier. This unit dose may be administered 1 to 5 times a day, so that a daily dose of from 0.5 to 25 000 mg, preferably 1 to 5000 mg, is administered.

If a solid composition is prepared in the form of tablets, the main ingredient is mixed with a pharmaceutical carrier such as gelatin, starch, lactose, magnesium stearate, talc, silicon dioxide or the like.

The tablets can be coated with sucrose, a cellulose derivative or another suitable substance, or be treated otherwise in order to display a sustained or delayed activity and in order to release a predetermined amount of the active basic ingredient continuously.

A preparation in the form of gelatin capsules is obtained by mixing the active ingredient with an extender and including the resulting mixture in soft or hard gelatin capsules.

A preparation in the form of a syrup or elixir or for administration in the form of drops may comprise active ingredients together with a sweetener, which is preferably calorie-free, methylparaben or propylparaben as antiseptics, a flavoring and a suitable color.

Water-dispersible powders or granules may comprise the active ingredients mixed with dispersants, wetting agents or suspending agents, such as polyvinylpyrrolidones, and sweeteners or masking flavors.

Rectal administration is achieved by using suppositories which are prepared with binders which melt at the rectal temperature, for example cocoa butter or polyethylene glycols. Parenteral administration is effected by using aqueous suspensions, isotonic saline solutions or sterile and injectable solutions which comprise pharmacologically acceptable dispersants and/or wetting agents, for example propylene glycol or polyethylene glycol.

The active basic ingredient may also be formulated as microcapsules or centrosomes, where suitable with one or more carriers or additives.

In addition to the compounds of the general formula (I) or their pharmaceutically acceptable salts, the inventive compositions may comprise other active basic ingredients which may be beneficial for the treatment of the disorders or diseases indicated above.

The present invention thus further relates to pharmaceutical compositions in which a plurality of active basic ingredients are present together, at least one of these being an inventive compound.

The inventive compounds represent antagonists of the so-called receptors of the vasopressin/oxytocin family. Such compounds can be investigated in suitable assays which ascertain the affinity for a receptor, where the affinity constant Ki represents a measure of the potency of the compounds and a smaller value represents a greater potency.

The inventive compounds have been tested for example for their receptor affinity for vasopressin receptors such as V1a and V1b, and in a cellular assay for their effect as antagonists of the effect mediated by vasopressin. The inventive compounds show surprisingly good effects therein.

Thus, Examples 2, 3, 4, 7, 8, 9, 10, 11, 12, 13, 14, 15, 16, 17, 18, 19, 20, 21, 25, 26, 27, 29, 30, 31, 32, 33, 34, 35, 36, 42, 43, 45, 46, 47, 48, 49 and 50 have shown good to very good affinities for the vasopressin V1b receptor, the measured Ki values being below 100 nM. In addition, some of these compounds show good selectivity vis-à-vis the other receptors of the vasopressin/oxytocin V1a, V2 and OT receptor family. This improved selectivity is regarded as advantageous and important because appreciable bindings to these receptors distinctly increases the risk of unwanted side effects.

The assays can be carried out for the inventive compounds for example in accordance with the assay procedures below.

Vasopressin V1a Receptor Binding Assay

The substances were dissolved in a concentration of $10^{-2}$ M in dimethyl sulfoxide (DMSO) and further diluted to $10^{-3}$ M to $10^{-9}$ M in DMSO. This DMSO predilution series was diluted 1:10 with assay buffer. The substance concentration was further diluted 1:10 in the assay mixture.

The binding assay was carried out by a method based on that of Tahara et al. (Tahara A et al., Brit. J. Pharmacol. 125, 1463-1470 (1998)). In the assay mixture (0.250 ml), membranes (50 μg of protein in incubation buffer (50 mM Tris, 10 mM $MgCl_2$, 0.1% BSA, adjusted to pH 7.4 with HCl)) from CHO cells with stably expressed human V1a receptors (preparation V1a clone 5.0, with protease inhibitors, Roche complete Mini #1836170) were incubated with 0.04 nM $^{125}$iodine-AVP (NEX128) in incubation buffer (total binding) or additionally with increasing concentrations of test substance (displacement experiment). The nonspecific binding was determined with $10^{-6}$ M AVP. Determinations in triplicate were carried out.

After incubation at room temperature for 60 minutes, the free radioligand was filtered off by vacuum filtration (Skatron cell harvester 7000) through Wathman GF/B glass fiber filter mats, and the filters were transferred into scintillation vials.

The liquid scintillation measurement took place in a model 2000 or 2200CA Tricarb instrument (Packard). Conversion of the measured cpm into dpm was carried out with the aid of a standard quench series.

The binding parameters were calculated by nonlinear regression in SAS. The algorithms of the program operate in analogy to the LIGAND analysis program (Munson P J and Rodbard D, Analytical Biochem. 107, 220-239 (1980)).

The affinities for the human vasopressin V1b receptor were measured, and affinity constants determined, in the above assay for the inventive examples.

Vasopressin V1b Receptor Binding Assay:

The substances were dissolved in a concentration of $10^{-2}$ M in DMSO and further diluted to $10^{-3}$ M to $10^{-9}$ M in DMSO. These DMSO solutions were diluted 1:10 with assay buffer. The substance concentration was further diluted 1:10 in the assay mixture.

The binding assay was carried out by a method based on that of Tahara et al. (Tahara A et al., Brit. J. Pharmacol. 125, 1463-1470 (1998)). In the assay mixture (0.250 ml), membranes (58 μg of protein in incubation buffer) from CHO-K1 cells with stably expressed human V1b receptors (preparation V1b-3H2, with protease inhibitors, Roche complete Mini #1836170) were incubated with 1.5 nM $^3$H-AVP (8-Arg-vasopressin, NET 800) in incubation buffer (50 mM Tris, 10 mM $MgCl_2$, 0.1% BSA, adjusted to pH 7.4 with HCl) (total binding) or additionally with increasing concentrations of test substance (displacement experiment). The nonspecific binding was determined with $10^{-6}$ M AVP. Determinations in triplicate were carried out.

Incubation buffer: 50 mM Tris, 10 mM $MgCl_2$, 0.1% BSA, adjusted to pH 7.4 with HCl.

After incubation at room temperature for 60 minutes, the free radioligand was filtered off by vacuum filtration (Skatron cell harvester 7000) through Wathman GF/B glass fiber filter mats, and the filters were transferred into scintillation vials.

The liquid scintillation measurement took place in a model 2000 or 2200CA Tricarb instrument (Packard). Conversion of the measured cpm into dpm was carried out with the aid of a standard quench series.

The binding parameters were calculated by nonlinear regression in SAS. The algorithms of the program operate in analogy to the LIGAND analysis program (Munson P J and Rodbard D, Analytical Biochem. 107, 220-239 (1980)).

The affinities for the human vasopressin V1b receptor were measured, and affinity constants determined, in the above assay for the inventive examples.

Vasopressin V2 Receptor Binding Assay:
Substances:

The test substances were dissolved in a concentration of $10^{-2}$ M in DMSO. The further dilution of these DMSO solutions took place in incubation buffer (50 mM Tris, 10 mM $MgCl_2$, 0.1% BSA, pH 7.4).

Membrane Preparation:

CHO-K1 cells with stably expressed human vasopressin V2 receptor (clone 23) were harvested and homogenized in 50 mM Tris-HCl and in the presence of protease inhibitors (Roche complete Mini #1836170) with a Polytron homogenizer at intermediate setting for 2×10 seconds, and subsequently centrifuged at 40 000×g for 1 h. The membrane pellet was again homogenized and centrifuged as described and subsequently taken up in 50 mM Tris-HCl, pH 7.4, homogenized and stored in aliquots frozen in liquid nitrogen at −190° C.

Binding Assay:

The binding assay was carried out by a method based on that of Tahara et al. (Tahara A et al., Brit. J. Pharmacol. 125, 1463-1470 (1998)).

Incubation buffer was: 50 mM Tris, 10 mM $MgCl_2$, 0.1% BSA, pH 7.4.

In assay mixture (250 μl), membranes (50 μg/ml protein in incubation buffer) from CHO-K1 cells with stably expressed human V2 receptors (cell line hV2__23_CHO) were incubated with 1-2 nM $^3$H-AVP (8-Arg-vasopressin, PerkinElmer #18479) in incubation buffer (50 mM Tris, 10 mM $MgCl_2$, 0.1% BSA, pH 7.4) (total binding) or additionally with increasing concentrations of test substance (displacement experiment). The nonspecific binding was determined with 1 μM AVP (Bachem #H1780). Determinations were carried out in triplicate.

After incubation at room temperature for 60 minutes, the free radioligand was filtered off by vacuum filtration (Skatron cell harvester 7000) through Wathman GF/B glass fiber filter mats, and the filters were transferred into scintillation vials.

The liquid scintillation measurement took place in a model 2000 or 2200CA Tricarb instrument (Packard). Conversion of the measured cpm into dpm was carried out with the aid of a standard quench series.

Evaluation:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^3$H-AVP for the recombinant hV2 receptors is 2.4 nM and was used to determine the Ki.

Oxytocin Receptor Binding Assay

The substances were dissolved in a concentration of $10^{-2}$ M in DMSO and diluted with incubation buffer (50 mM Tris, 10 mM $MgCl_2$, 0.1% BSA, pH 7.4).

Confluent HEK-293 cells with transiently expressing recombinant human oxytocin receptors were centrifuged at 750×g at room temperature for 5 minutes. The residue was taken up in ice-cold lysis buffer (50 mM Tris-HCl, 10% glycerol, pH 7.4 and Roche complete protease inhibitor) and subjected to an osmotic shock at 4° C. for 20 minutes. The lyzed cells were then centrifuged at 750×g at 4° C. for 20 minutes, the residue was taken up in incubation buffer, and aliquots of $10^7$ cells/ml were prepared. The aliquots were frozen at −80° C. until used.

On the day of the experiment, the cells were thawed, diluted with incubation buffer and homogenized using a Multipette Combitip (Eppendorf, Hamburg). The reaction mixture of 0.250 ml was composed of 2 to 5×$10^4$ recombinant cells, 3-4 nM $^3$H-oxytocin (PerkinElmer, NET 858) in the presence of test substance (inhibition plot) or only incubation buffer (total binding). The nonspecific binding was determined with $10^{-6}$ M oxytocin (Bachem AG, H2510). Determinations in triplicate were set up. Bound and free radioligand were separated by filtration under vacuum with Whatman GF/B glass fiber filters using a Skatron cell harvester 7000. The bound radioactivity was determined by liquid scintillation measurement in a Tricarb beta counter, model 2000 or 2200CA (Packard).

The binding parameters were calculated by nonlinear regression analysis (SAS), in analogy to the LIGAND program of Munson and Rodbard (Analytical Biochem 1980; 107: 220-239). The Kd of $^3$H-oxytocin for the recombinant hOT receptors is 7.6 nM and was to determine the Ki.

Effect on Vasopressin-Induced Calcium Increase in Cells Having a Cloned Human Vasopressin Receptor The functional activity of the test substances was investigated on CHO-K1 cells which were stably transfected with the human V1b receptor. 50 000 cells were seeded in each well of a microtiter plate with 96 wells and incubated in culture medium in a saturated water vapor atmosphere with 5% $CO_2$ at 37° C. overnight. The culture medium consisted of DMEM/Nut Mix F12 with Glutamax I (from Invitrogen), 10% fetal calf serum, 100 units/ml penicillin, 100 μg/ml streptomycin and 800 μg/ml Geneticin. The following day, the cells were washed with culture medium and loaded with a fluorescent dye for calcium in accordance with the manufacturer's statements ($Ca^{++}$-Plus-Assay Kit, Molecular Devices). The cells were loaded in the presence of probenzid (1 vol %). The test substances were diluted with culture medium (final concentration $10^{-10}$ to $10^{-5}$M) and incubated with the dye-loaded cells at room temperature for 15 minutes. The Arg-vasopressin ($10^{-8}$M) was added and the maximum fluorescence signal was determined using a FLIPR-96 measuring instrument (Molecular Devices). Concentration-effect plots were constructed using nonlinear regression algorithms (GraphPad Prism 3.0). Kb values were calculated from IC50 values by the method of Cheng and Prusoff (Kb=IC50/1+L/EC50).

The affinities of the compounds (I) of the invention for the human vasopressin V1b receptor were measured in accordance with the above assays, and the affinity constants (Ki) were determined. Table 1 below details the V1b receptor affinity of selected compounds (+++ means <10 nM and ++ means 10-100 nM).

TABLE 1

| Example | V1b Ki |
|---------|--------|
| 2  | ++  |
| 3  | +++ |
| 4  | +++ |
| 7  | ++  |
| 8  | ++  |
| 9  | ++  |
| 10 | +++ |
| 11 | ++  |
| 12 | +++ |
| 13 | ++  |
| 14 | +++ |
| 15 | +++ |
| 16 | +++ |
| 17 | +++ |
| 18 | ++  |
| 19 | +++ |
| 20 | +++ |
| 21 | ++  |

TABLE 1-continued

| Example | V1b Ki |
|---------|--------|
| 25 | ++  |
| 26 | +++ |
| 27 | ++  |
| 29 | ++  |
| 30 | +++ |
| 31 | +++ |
| 32 | ++  |
| 33 | +++ |
| 34 | +++ |
| 35 | ++  |
| 42 | ++  |
| 43 | ++  |
| 45 | ++  |
| 46 | ++  |
| 47 | ++  |
| 48 | ++  |
| 50 | ++  |

It is additionally possible in accordance with the above assays to determine the affinities for further vasopressin receptors or their subtypes such as, for example, V1a and V2, and the oxytocin (OT) receptor. The quotients obtainable thereby for the corresponding Ki values, i.e. "Ki(V1a)/Ki (V1b)", "Ki(V2)/Ki(V1b)" and/or "Ki(OT)Ki(V1b)", may serve as a measure of a possible selectivity of the compounds of the invention in relation to a particular vasopressin or oxytocin receptor or one of their subtypes such as, for example, V1b.

Examples of synthetic routes for preparing the inventive compounds are described below.

The inventive oxindoles can be prepared in various ways as outlined in synthesis schemes 1-4. The variables in these synthesis schemes have the same meanings as in the general formula (I).

SYNTHESIS SCHEME 1

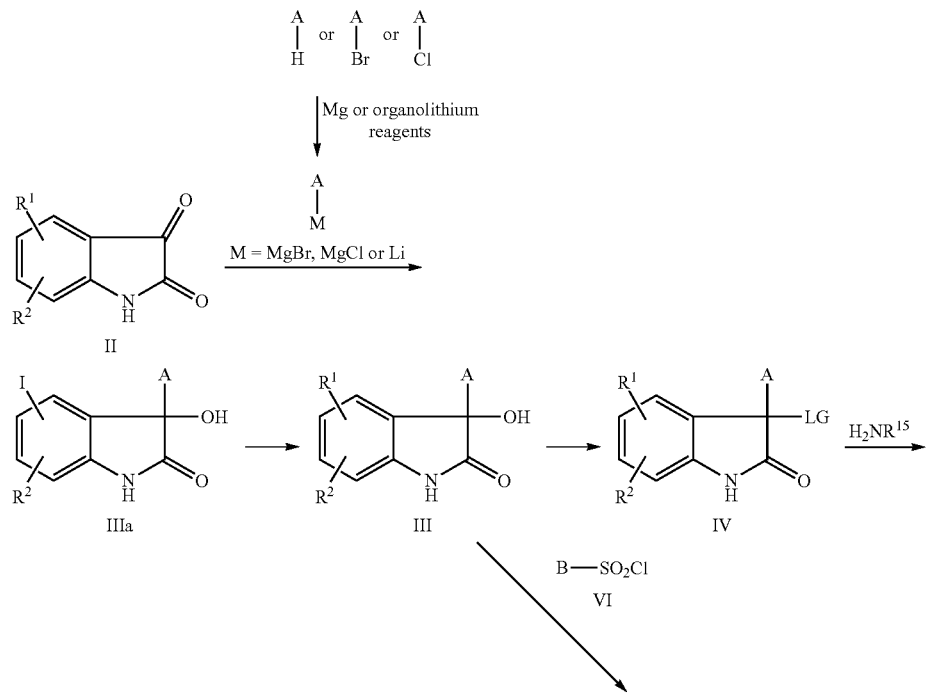

-continued

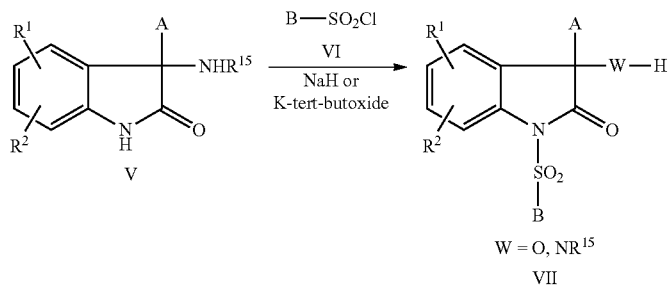

W = O, NR$^{15}$
VII

LG = leaving group

Starting from compounds A-H or A-Br or A-Cl, which are metallated in a conventional way such as, for example, as Grignard compound or organyllithium compound, it is possible to obtain the 3-hydroxyoxindoles IIIa by addition onto isatins II. The metallated compounds can be obtained in a conventional way from halo- or hydrocarbon compounds. Exemplary methods are present in Houben-Weyl, Methoden zur Organischen Chemie, vol. 13, 1-2, chap. Mg and Li compounds. The isatins II are either commercially available or were prepared in analogy to methods described in the literature (Advances in Heterocyclic Chemistry, A. R. Katritzky and A. J. Boulton, Academic Press, New York, 1975, 18, 2-58; J. Brazil. Chem. Soc. 12, 273-324, 2001).

The 3-hydroxyoxindoles IIIa which comprise an iodine in the 6-membered aromatic ring can be converted into the analogous cyano-containing 3-hydroxyoxindoles III with KCN and with Pd(0) catalysis in solvents such as dimethylformamide with the addition of bases such as $K_2CO_3$ or other carbonates and amines at elevated temperature. The Pd(0) salts which can be taken are for example transition metal complexes which are prepared in situ from $PdCl_2$ or $PdOAc_2$ by adding phosphines such as tris(orthotolyl)phosphine. It is likewise possible to employ commercial palladium complexes or phosphine ligands.

The 3-hydroxyoxindoles III can be converted into the compounds IV which have a leaving group LG in position 3, possibilities for the leaving group LG being conventional leaving groups such as, for example, halides, mesylate or tosylate. Thus, for example (LG=chlorine), the intermediate IV can be prepared by treating the alcohol III with thionyl chloride in the presence of a base such as, for example, pyridine. Alternatively, alcohols III can be obtained by conversion into the mesylate using methanesulfonyl chloride in the presence of a base such as, for example, triethylamine. The compounds IV are subsequently reacted with amines $NH_2R^{15}$, resulting in the analogous amines V. For example, such substitution reactions with amine in the presence of a base such as N,N-diisopropylethylamine can result in the analogous 3-aminooxindoles V. V can subsequently take place by treatment with sulfonyl chlorides VI after deprotonation with a strong base such as, for example, potassium tert-butoxide or sodium hydride in DMF, and be converted into the product VII. The corresponding derivatives VII with W=O can be obtained in an analogous manner starting from the alcohols III.

SYNTHESIS SCHEME 2

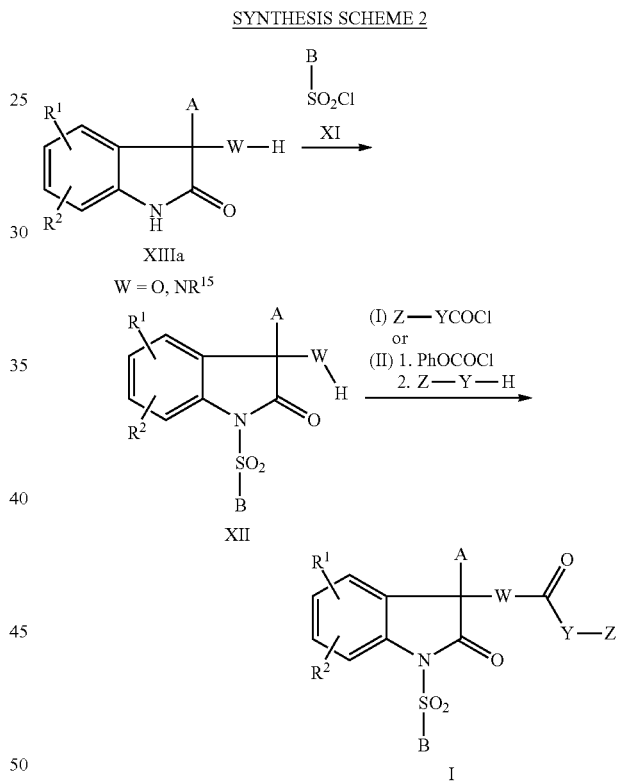

The inventive compounds I are prepared by initially reacting the oxindoles XIIIa with sulfonyl chlorides XI under the conditions already described above. The sulfonyl chlorides XI employed can either be acquired by purchase or be prepared in an analogous manner to known processes (see, for example, J. Med. Chem. 40, 1149 (1997)). The inventive compounds I are prepared in various ways starting from the sulfonylated compounds XII: (i) reaction with carbamoyl chlorides Z—Y—CO—Cl in the presence of a base such as, for example, triethylamine; (ii) activation with phenyl chloroformate in the presence of a base such as, for example, pyridine and subsequent reaction with amines Z—Y—H, if appropriate at elevated temperatures. The amines Z—Y—H can either be acquired by purchase or be prepared by methods known from the literature.

Inventive compounds I which have a functionalized nitrogen atom in position 3 (e.g. amides, sulfonamides, carbamates and ureas) are prepared in analogy to synthesis scheme 2: the 3-aminooxindoles XII (W=NR$^{15}$) are converted by reaction with reagents for derivatizing amino groups, such as, for example, carboxylic acids, carbonyl chlorides, carboxylic anhydrides, sulfonyl chlorides, chloroformates, isocyanates or carbamoyl chlorides, into the inventive compounds I, generally making use of conventional methods (see J. March, Advanced Organic Chemistry, 1992, 4th edition, Wiley, New York, p. 417-421; 499; 903). It is additionally possible for the 3-amino group in the compounds XII (W=NH) to be substituted by treatment with alkylating agents such as, for example, alkyl bromides, iodides or mesylates, and by reaction with aldehydes or ketones in the presence of reducing agents such as, for example, sodium cyanoborohydride, in the manner of a reductive amination (J. March, Advanced Organic Chemistry, 1992, 4th edition, Wiley, New York, p. 411; 898).

Alternatively, the building blocks XII can be prepared by the two-stage process shown in the synthesis scheme 3.

SYNTHESIS SCHEME 3

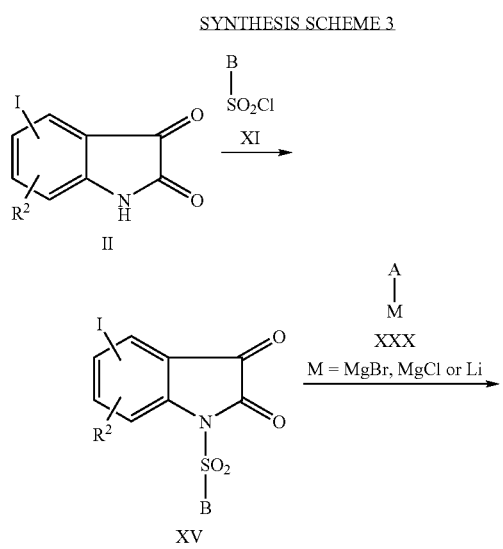

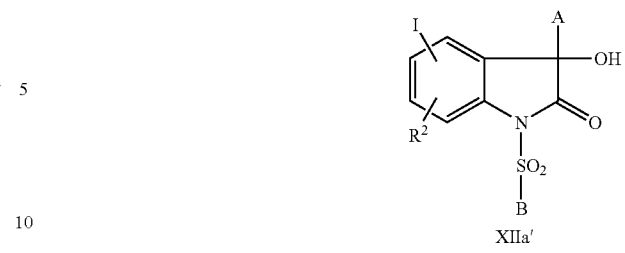

XIIa'

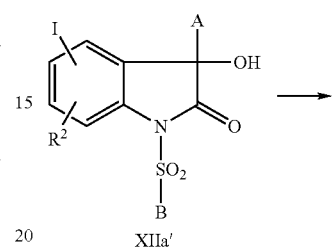

XIIa'

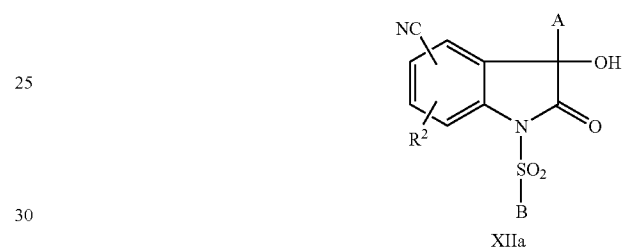

XIIa

Sulfonylated isatins XV are obtained by deprotonation of isatins II with a strong base such as, for example, sodium hydride or potassium tert-butanolate, and subsequent treatment with sulfonyl chlorides XI. The compounds XIIa' are obtained in the second step by addition of metallated compounds XXX onto the 3-keto group of the sulfonylisatins XV. Introduction of cyanide with KCN is possible in analogy to synthesis scheme 1 to give the product XIIa. The methods are analogous to the processes described above.

SYNTHESIS SCHEME 4

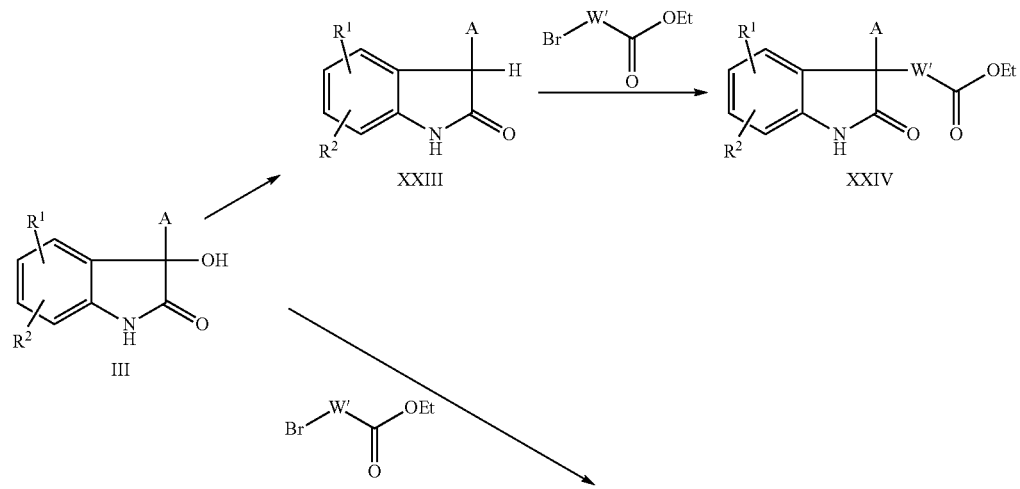

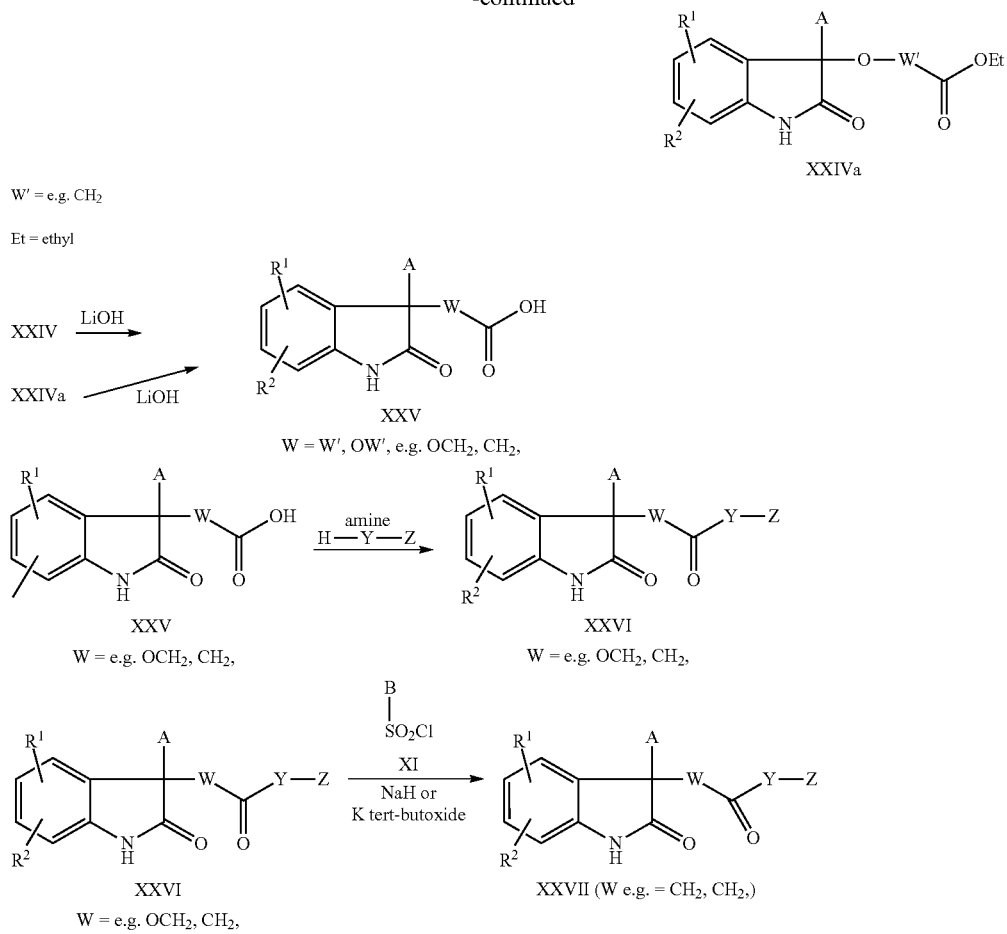

Routes to compounds in which W can be varied are outlined in synthesis scheme 4. Alcohols III are reacted with halo carboxylic esters to give the derivatives XXIV or XXIVa, preferably using bromides or chlorides, although analogous mesylates or tosylates and similar compounds in which a leaving group is present can be used. The reactions can be carried out for example in polar solvents such as DMF or THF, with the addition of basic substances such as, for example, NaH, potassium tert-butanolate, sodium ethanolate, trialkylamines or potassium carbonate, at room temperature or elevated temperatures such as the boiling point of the solvent. Reaction of the indol-2-one XXIII to give XXIV is carried out analogously. The indolones XXIII can be prepared synthetically either from the analogous alcohols III by reducing the alcohol group, for example with triethylsilane or in analogy to Mullock, E. B. et al., J. Chem. Soc. C, 1970, 6, 829-833, Ghosal, S. et al., Ind. J. Chem., 1969m 7, 1095-1097 and U.S. Pat. No. 2,759,935. The esters XXIV or XXIVa can be converted with acids such as HCl and $H_2SO_4$ or bases such as NaOH, KOH or LiOH into the analogous carboxylic acids XXV, normally operating in solvents such as alcohols or THF, with the addition of aqueous acids or bases at room temperature or temperatures of 25-70° C. These acids XXV can be converted into the derivatives XXVI by reacting the acids with, for example, amines by using conventional coupling conditions as detailed for example in R. C. Larock, Comprehensive Organic Transformations, Wiley 1999, Chap. 9. Introduction of the sulfonic acid residue B—$SO_2$— takes place in a manner analogous to that described above. As alternative to scheme 4, the last two steps can also be carried out in the reverse order.

EXPERIMENTAL SECTION

Example 1

5-Cyano-1-(2,4-dimethoxybenzenesulfonyl)-3-(2-ethoxyphenyl)-2-oxo-2,3-dihydro-1H-indol-3-yl 4-(6-methylpyridin-2-yl)piperazine-1-carboxylate 1a) 3-(2-Ethoxyphenyl)-3-hydroxy-5-iodoindol-2-one 4 g (164 mmol) of magnesium turnings and 5% of the total amount of 2-bromo-1-ethoxybenzene were put into 20 ml of ether and, after addition of a little iodine, were heated until the reaction started. 33.1 g (165 mmol) of 2-bromo-1-ethoxybenzene dissolved in 100 ml of ether were slowly added dropwise to the boiling solution in such a way that the reaction continued with gentle boiling. Then, while cooling slightly to 20° C., 15 g (54.9 mmol) of 5-iodoisatin in 400 ml of anhydrous tetrahydrofuran were added dropwise. The mixture was then stirred at room temperature for 2 h. The reaction solution was poured into an aqueous $NH_4Cl$ solution with stirring. This aqueous phase was extracted several times with ethyl acetate, and the combined aqueous phase was washed four times with water, dried and concentrated in vacuo, resulting in the product as a crystalline precipitate. 19.2 g of the product were obtained.

1b) 5-Cyano-3-(2-ethoxyphenyl)-3-hydroxy-indol-2-one 37.2 g (94 mmol) of the product 1a and 11.1 g (94 mmol) of zinc cyanide in 300 ml of DMF were heated to 95° C. Then 1.6 g (1.38 mmol) of tetrakis(triphenylphosphine)palladium(0) were added in portions every 10 minutes. After 45 minutes, the reaction mixture was poured into ice-water and extracted with ethyl acetate. The organic phase was washed with saturated NaCl solution, dried and concentrated in vacuo. The residue obtained in this way crystallizes from a little ethyl acetate. 24 g of the product were obtained.

1c) 5-Cyano-1-(2,4-dimethoxybenzenesulfonyl)-3-hydroxy-3-(2-ethoxyphenyl)-indol-2-one 1.7 g (15 mmol) of potassium tert-butanolate were added in portions to 4 g (13.6 mmol) of the intermediate 1b in 40 ml of anhydrous dimethylformamide at 0° C., and the mixture was stirred for about 90 minutes. Then 3.4 g (14.3 mmol) of 2,4-dimethoxybenzenesulfonyl chloride were rapidly added dropwise at 0° C. The reaction mixture was stirred at 0° C. for 2 h. This solution was then poured into an ice-water/$K_2CO_3$ solution, resulting in a precipitate which was isolated. The resulting residue was treated with a little methanol, filtered off with suction and dried, resulting in 3.3 g of the product.

1d) 5-Cyano-1-(2,4-dimethoxybenzenesulfonyl)-3-(2-ethoxyphenyl)-2-oxo-2,3-dihydro-1-H-indol-3-yl phenyl carbonate 1.5 g (3.0 mmol) of the product 1c were dissolved in 30 ml of pyridine. At 0° C., 1.7 g (10.6 mmol) of phenyl chloroformate were rapidly added dropwise. This reaction solution was stirred for 60 minutes before being stirred into ice-water. The resulting precipitate was isolated, dissolved in methylene chloride, dried and concentrated in vacuo. The resulting residue was crystallized with $Et_2O$/n-pentane. 1.2 g of the intermediate were obtained.

1e) 5-Cyano-1-(2,4-dimethoxybenzenesulfonyl)-3-(2-ethoxyphenyl)-2-oxo-2,3-dihydro-1H-indol-3-yl 4-(6-methylpyridin-2-yl)piperazine-1-carboxylate 0.1 g (0.16 mmol) of intermediate 1d and 115 mg (0.65 mmol) of 1-(6-methylpyridin-2-yl)piperazine were stirred in 3 ml of DMF at 100° C. for 20 minutes. The reaction mixture was then poured into 30 ml of ice-water/$K_2CO_3$. The resulting precipitate was isolated and crystallized from a little methanol, resulting 0.1 g of the product.

$^1$H-NMR (CDCl$_3$): δ=1.25 (3H), 2.4 (3H), 3.2-3.9 (15H), 4.05 (1H), 6.4 (2H), 6.55 (2H), 6.7 (1H), 7.0 (1H), 7.2-7.4 (3H), 7.65 (1H), 7.7 (1H), 8.05 (1H) and 8.15 (1H) ppm.

The following compounds were prepared in an analogous manner to Example 1 using methodological processes analogous to the described methods:

Example 2

5-Cyano-1-(2-methoxybenzenesulfonyl)-3-(2-ethoxyphenyl)-2-oxo-2,3-dihydro-1H-indol-3-yl 4-(pyridin-4-yl)piperazine-1-carboxylate $^1$H-NMR (CDCl$_3$): δ=1.25 (3H), 3.1-3.5 (6H), 3.6 (3H), 3.65-3.9 (3H), 4.1 (1H), 6.6 (2H), 6.8 (1H), 6.95 (1H), 7.0 (2H), 7.25 (1H), 7.3 (1H), 7.55 (2H), 7.7 (2H), 8.15 (2H) and 8.3 (2H) ppm.

Example 3

5-Cyano-1-(2,4-dimethoxybenzenesulfonyl)-3-(2-ethoxyphenyl)-2-oxo-2,3-dihydro-1H-indol-3-yl 4-(pyridin-4-yl)piperazine-1-carboxylate $^1$H-NMR (CDCl$_3$): δ=1.2 (3H), 3.2-3.5 (6H), 3.55 (3H), 3.7-3.9 (6H), 4.05 (1H), 6.4 (1H), 6.5 (1H), 6.6 (2H), 6.8 (1H), 7.0 (1H), 7.25 (1H), 7.3 (1H), 7.65 (2H), 8.05 (1H), 8.1 (1H) and 8.3 (2H) ppm.

Example 4

5-Cyano-1-(2-methoxybenzenesulfonyl)-3-(2-ethoxyphenyl)-2-oxo-2,3-dihydro-1H-indol-3-yl 4-(thiazol-2-yl)piperazine-1-carboxylate $^1$H-NMR (CDCl$_3$): δ=1.25 (3H), 3.1-3.9 (12H), 4.05 (1H), 6.6 (1H), 6.8 (1H), 6.9 (1H), 7.05 (2H), 7.2 (1H), 7.25-7.35 (2H), 7.55 (2H), 7.65 (2H) and 8.15 (2H) ppm.

Example 5

5-Cyano-1-(2-methoxybenzenesulfonyl)-3-(2-ethoxyphenyl)-2-oxo-2,3-dihydro-1H-indol-3-yl 4-(5-cyanopyridin-2-yl)piperazine-1-carboxylate $^1$H-NMR (CDCl$_3$): δ=1.25 (3H), 3.2 (2H), 3.45 (2H), 3.6 (3H), 3.65-3.9 (5H), 4.05 (1H), 6.55 (1H), 6.85 (1H), 6.95 (1H), 7.05 (2H), 7.25 (1H), 7.3 (1H), 7.55 (1H), 7.65 (2H), 8.15 (2H) and 8.4 (1H) ppm.

Example 6

5-Cyano-1-(4-chlorobenzenesulfonyl)-3-(2-ethoxyphenyl)-2-oxo-2,3-dihydro-1H-indol-3-yl 4-(5-cyanopyridin-2-yl)piperazine-1-carboxylate $^1$H-NMR (CDCl$_3$): δ=1.25 (3H), 3.15 (2H), 3.5 (2H), 3.55-3.9 (5H), 4.0 (1H), 6.55 (1H), 6.8 (1H), 7.05 (1H), 7.25 (1H), 7.35 (1H), 7.45 (2H), 7.65 (3H), 8.0-8.15 (3H) and 8.4 (1H) ppm.

Example 7

5-Cyano-1-(2,4-difluorobenzenesulfonyl)-3-(2-ethoxyphenyl)-2-oxo-2,3-dihydro-1H-indol-3-yl 4-(pyridin-4-yl)piperazine-1-carboxylate $^1$H-NMR (CDCl$_3$): δ=1.25 (3H), 3.1-3.5 (6H), 3.65-3.85 (3H), 4.05 (1H), 6.65 (2H), 6.8 (1H), 6.9 (1H), 7.0 (2H), 7.3 (1H), 7.35 (1H), 7.7 (2H), 8.15 (2H) and 8.3 (2H) ppm.

Example 8

5-Cyano-1-(2-fluorobenzenesulfonyl)-3-(2-ethoxyphenyl)-2-oxo-2,3-dihydro-1H-indol-3-yl 4-(pyridin-4-yl)piperazine-1-carboxylate $^1$H-NMR (CDCl$_3$): δ=1.25 (3H), 3.2-3.5 (6H), 3.65 (3H), 4.1 (1H), 6.6 (2H), 6.8 (1H), 7.05 (2H), 7.20 (1H), 7.25 (1H), 7.3 (2H), 7.65 (1H), 7.7 (2H), 8.15 (2H) and 8.3 (2H) ppm.

Example 9

5-Cyano-1-benzenesulfonyl-3-(2-ethoxyphenyl)-2-oxo-2,3-dihydro-1H-indol-3-yl 4-(pyridin-4-yl)-piperazine-1-carboxylate $^1$H-NMR (CDCl$_3$): δ=1.2 (3H), 3.1-3.25 (4H), 3.3-3.5 (2H), 3.65-3.85 (3H), 4.0 (1H), 6.6 (2H), 6.8 (1H), 7.05 (1H), 7.25 (1H), 7.35 (1H), 7.50 (2H), 7.6-7.75 (3H), 8.05-8.2 (3H) and 8.3 (2H) ppm.

Example 10

4-(Pyridin-4-yl)piperazine-1-[1-(2-methoxybenzenesulfonyl)-5-cyano-2-oxo-3-(2-ethoxyphenyl)-2,3-dihydro-1H-indol-3-yl]carboxamide

10a) 3-Amino-5-cyano-3-(2-ethoxyphenyl)indol-2-one 8.0 g (27.2 mmol) of intermediate 1b and 43 ml (54.4 mmol) of pyridine were dissolved in 70 ml of methylene chloride. Then, at 0° C., 3 ml (40.8 mmol) of SOCl$_2$ were slowly added dropwise. The reaction mixture was then stirred for a further 30 minutes. The reaction solution was subsequently poured into ice-water, and the organic phase was separated off, washed with water, dried and concentrated in vacuo. This residue was added at 0° C. to a solution of 300 ml of 0.5M NH$_3$ solution in dioxane and 150 ml of methylene chloride. The mixture was stirred at room temperature for 16 h. The reaction solution was concentrated in vacuo, and the residue obtained in this way was suspended in water. The precipitate was separated off and recrystallized from a little methanol. 4.7 g of the product were obtained.

10b) Phenyl[5-cyano-3-(2-ethoxyphenyl)-2-oxo-2,3-dihydro-1H-indol-3-yl]-carbamate 1.2 ml (9.38 mmol) of phenyl chloroformate were added dropwise to 2.5 g (8.5 mmol) of product 10a dissolved in 50 ml of pyridine at 0° C. The reaction solution was then stirred at room temperature for 16 h. The solution was subsequently poured into ice-water, and the aqueous phase was extracted with ethyl acetate (AcOEt). The organic phase was washed several times with water, dried and concentrated in vacuo. 3.9 g of the product were obtained.

10c) 4-Pyridin-4-ylpiperazine-1-[5-cyano-3-(2-ethoxyphenyl)-2-oxo-2,3-dihydro-1H-indol-3-yl]carboxamide 4 g (8.5 mmol) of intermediate 10b and 5.6 (34.1 mmol) of 1-(4-pyridyl)piperazine in 70 ml of tetrahydrofuran were stirred at room temperature for 16 h. The solvent was then removed in vacuo. The residue was partitioned between water and ethyl acetate. The aqueous phase was washed twice with ethyl acetate. The combined ethyl acetate phases were again washed with water, dried and concentrated in vacuo. The residue was dissolved in a little ethanol, and this solution was added dropwise to ether, resulting in a solid which was isolated. 1.9 g of the product were obtained.

10d) 4-Pyridin-4-ylpiperazine-1-[5-cyano-3-(2-ethoxyphenyl)-1-(2-methoxybenzenesulfonyl)-2-oxo-2,3-dihydro-1H-indol-3-yl]carboxamide dihydrochloride 51 mg (0.46 mmol) of potassium tert-butanolate were added in portions to 200 mg (0.41 mmol) of intermediate 10c in 4 ml of anhydrous dimethylformamide at 0° C., and the mixture was stirred for about 60 minutes. Subsequently, 94 mg (0.46 mmol) of 2-methoxybenzenesulfonyl chloride were added at 0° C. The mixture was stirred at room temperature for 16 h. The reaction solution was then poured into 1M NaOH, resulting in a precipitate which was isolated. This precipitate was purified by chromatography on silica gel (eluent: CH$_2$Cl$_2$/CH$_3$OH=9/1). The product obtained in this way was dissolved in a little methanol and mixed with ethereal HCl, whereupon the product precipitated as dihydrochloride. The precipitate was isolated to result in 120 mg of the product as dihydrochloride.

$^1$H-NMR (CDCl$_3$): δ=1.15 (3H), 3.3-3.5 (7H), 3.55-3.75 (4H), 3.85 (1H), 4.05 (1H), 6.95 (1H), 7.0 (1H), 7.1-7.3 (4H), 7.35 (2H), 7.7 (2H), 7.8 (2H), 7.9 (1H), 8.0 (1H), 8.25 (2H) and about 13.6 (broad, N$^+$H) ppm.

The following compounds were prepared in an analogous manner to Examples 1 and 10 using methodological processes analogous to the described methods:

Example 11

4-(Pyridin-4-yl)piperazine-1-[1-benzenesulfonyl-5-cyano-2-oxo-3-(2-ethoxyphenyl)-2,3-dihydro-1H-indol-3-yl]carboxamide $^1$H-NMR (CDCl$_3$): δ=1.5 (3H), 3.25-3.5 (8H), 4.1 (1H), 4.2 (1H), 6.6 (3H), 6.9 (2H), 7.0 (1H), 7.3 (1H), 7.5 (3H), 7.6 (2H), 8.05 (1H), 8.15 (2H) and 8.3 (2H) ppm.

Example 12

4-(Pyridin-4-yl)piperazine-1-[1-(2-fluorobenzenesulfonyl)-5-cyano-2-oxo-3-(2-ethoxyphenyl)-2,3-dihydro-1H-indol-3-yl]carboxamide $^1$H-NMR (CDCl$_3$): δ=1.5 (3H), 3.2-3.5 (8H), 4.1 (1H), 4.2 (1H), 6.6 (3H), 6.9 (2H), 7.1 (1H), 7.2 (1H), 7.2-7.4 (2H), 7.55 (2H), 7.6 (2H), 8.15 (1H), 8.2 (1H) and 8.3 (2H) ppm.

Example 13

4-(Pyridin-4-yl)piperazine-1-[1-(2,4-difluorobenzenesulfonyl)-5-cyano-2-oxo-3-(2-ethoxyphenyl)-2,3-dihydro-1H-indol-3-yl]carboxamide $^1$H-NMR (CDCl$_3$): δ=1.5 (3H), 3.2-3.5 (8H), 4.1 (1H), 4.2 (1H), 6.55 (1H), 6.6 (2H), 6.85-7.05 (3H), 7.1 (1H), 7.25 (1H), 7.3 (1H), 7.5 (1H), 7.65 (1H), 8.1 (1H), 8.2 (1H) and 8.3 (2H) ppm.

Example 14

4-(Pyridin-4-yl)piperazine-1-[1-(4-cyanobenzenesulfonyl)-5-cyano-2-oxo-3-(2-ethoxyphenyl)-2,3-dihydro-1H-indol-3-yl]carboxamide $^1$H-NMR (CDCl$_3$): δ=1.1 (3H), 3.15-3.4 (8H), 3.8 (1H), 3.95 (1H), 6.8 (2H), 6.95 (1H), 7.05 (1H), 7.35 (1H), 7.55 (1H), 7.7 (1H), 7.8 (2H), 7.9 (1H) and 8.1-8.25 (6H) ppm.

Example 15

4-(Pyridin-4-yl)piperazine-1-[1-(2-methoxy-4-methylbenzenesulfonyl)-5-cyano-2-oxo-3-(2-ethoxyphenyl)-2,3-dihydro-1H-indol-3-yl]carboxamide $^1$H-NMR (CDCl$_3$): δ=1.5 (3H), 2.4 (3H), 3.35 (4H), 3.45 (3H), 3.55 (3H), 4.1-4.3 (2H), 6.6 (2H), 6.7 (1H), 6.8-7.0 (5H), 7.3 (1H), 7.6 (2H), 8.0 (1H), 8. (1H) and 8.3 (2H) ppm.

Example 16

4-(Pyridin-4-yl)piperazine-1-[1-(2,4-dimethoxybenzenesulfonyl)-5-cyano-2-oxo-3-(2-ethoxyphenyl)-2,3-dihydro-1H-indol-3-yl]carboxamide $^1$H-NMR (CDCl$_3$): δ=1.3 (3H), 3.3 (4H), 3.45 (3H), 3.5 (3H), 4.15-4.3 (2H), 6.4 (1H), 6.55 (1H), 6.8-6.9 (2H), 6.95 (2H), 7.3 (1H), 7.6 (2H), 8.1 (2H) and 8.3 (2H) ppm.

Example 17

4-(Pyridin-4-yl)piperazine-1-[1-(4-nitrobenzenesulfonyl)-5-cyano-2-oxo-3-(2-ethoxyphenyl)-2,3-dihydro-1H-indol-3-yl]carboxamide $^1$H-NMR (CDCl$_3$): δ=1.5 (3H), 3.2-3.4 (8H), 4.1 (1H), 4.2 (1H), 6.5 (1H), 6.6 (2H), 6.95 (2H), 7.15 (1H), 7.35 (1H), 7.45 (1H), 7.65 (1H), 8.05 (1H) and 8.2-8.4 (6H) ppm.

Example 18

1-(4-Cyanobenzenesulfonyl)-5-cyano-2-oxo-3-(2-ethoxyphenyl)-2,3-dihydro-1H-indol-3-yl 4-(pyridin-4-yl)piperazine-1-carboxylate $^1$H-NMR (CDCl$_3$): δ=1.25 (3H), 3.1-3.3 (4H), 3.3-3.5 (2H), 3.7-3.9 (3H), 4.05 (1H), 6.65 (2H), 6.8 (1H), 7.05 (1H), 7.25 (1H), 7.35 (1H), 7.7 (2H), 7.8 (2H), 8.1 (1H), 8.2 (2H) and 8.3 (2H) ppm.

Example 19

1-(4-Nitrobenzenesulfonyl)-5-cyano-2-oxo-3-(2-ethoxyphenyl)-2,3-dihydro-1H-indol-3-yl 4-(pyridin-4-yl)piperazine-1-carboxylate $^1$H-NMR (CDCl$_3$): δ=1.3 (3H), 3.0-3.25 (4H), 3.35 (2H), 3.7 (2H), 3.8 (1H), 4.05 (1H), 6.6 (2H), 6.8 (1H), 7.05 (1H), 7.25 (1H), 7.35 (1H), 7.7 (2H), 8.05 (2H), 8.1 (1H) and 8.2-8.4 (6H) ppm.

Example 20

[1-(2-Methoxy-4-methylbenzenesulfonyl)-5-cyano-2-oxo-3-(2-ethoxyphenyl)-2,3-dihydro-1H-indol-3-yl 4-(pyridin-4-yl)piperazine-1-carboxylate $^1$H-NMR (CDCl$_3$): δ=1.2 (3H), 2.4 (3H), 3.2-3.5 (6H), 3.55 (3H), 3.7 (2H), 3.8 (1H), 4.05 (1H), 6.6 (2H), 6.7 (1H), 6.8 (1H), 6.85 (1H), 7.0 (1H), 7.25 (1H), 7.3 (1H), 7.65 (2H), 8.0 (1H), 8.15 (1H) and 8.3 (2H) ppm.

Example 21

1-(4-Fluorobenzenesulfonyl)-5-cyano-2-oxo-3-(2-ethoxyphenyl)-2,3-dihydro-1H-indol-3-yl 4-(pyridin-4-yl)piperazine-1-carboxylate $^1$H-NMR (CDCl$_3$): δ=1.25 (3H), 3.2-3.3 (4H), 3.3-3.5 (2H), 3.7-3.9 (3H), 4.0 (1H), 6.6 (2H), 6.8 (1H), 7.05 (1H), 7.2 (2H), 7.25 (1H), 7.3 (1H), 7.7 (2H), 8.1 (1H), 8.15 (2H) and 8.3 (2H) ppm.

Example 22

1-(2,4-Dimethoxybenzenesulfonyl)-5-cyano-2-oxo-3-(2-ethoxyphenyl)-2,3-dihydro-1H-indol-3-yl 4-(3-cyanopyridin-2-yl)piperazine-1-carboxylate $^1$H-NMR (CDCl$_3$): δ=1.25 (3H), 3.25 (2H), 3.4-3.9 (13H), 4.05 (1H), 6.4 (1H), 6.55 (1H), 6.8 (2H), 7.05 (1H), 7.3 (2H), 7.65 (2H), 7.8 (1H), 8.05 (1H), 8.15 (1H) and 8.35 (1H) ppm.

Example 23

1-(2,4-Dimethoxybenzenesulfonyl)-5-cyano-2-oxo-3-(2-ethoxyphenyl)-2,3-dihydro-1H-indol-3-yl 4-(3-methylpyridin-2-yl)piperazine-1-carboxylate $^1$H-NMR (CDCl$_3$): δ=1.2 (3H), 2.3 (3H), 3.0 (2H), 3.1-3.4 (4H), 3.55 (3H), 3.7-3.9 (6H), 4.05 (1H), 6.4 (1H), 6.55 (1H), 6.8 (1H), 6.9 (1H), 7.0 (1H), 7.3 (2H), 7.4 (1H), 7.65 (1H), 7.7 (1H), 8.05 (1H) and 8.15 (2H) ppm.

Example 24

1-(2,4-Dimethoxybenzenesulfonyl)-5-cyano-2-oxo-3-(2-ethoxyphenyl)-2,3-dihydro-1H-indol-3-yl 4-(4-methylpyridin-2-yl)piperazine-1-carboxylate $^1$H-NMR (CDCl$_3$): δ=1.2 (3H), 2.25 (3H), 3.2 (2H), 3.35 (2H), 3.45-3.7 (5H), 3.75 (2H), 3.8 (1H), 3.85 (3H), 4.05 (1H), 6.4 (2H), 6.5 (2H), 6.8 (1H), 7.0 (1H), 7.3 (2H), 7.6-7.7 (2H), 8.05 (2H) and 8.1 (1H) ppm.

Example 25

1-(2,4-Dimethoxybenzenesulfonyl)-5-cyano-2-oxo-3-(2-ethoxyphenyl)-2,3-dihydro-1H-indol-3-yl 4-(pyridin-2-yl)piperazine-1-carboxylate $^1$H-NMR (CDCl$_3$): δ=1.2 (3H), 3.2-3.9 (15H), 4.05 (1H), 6.4 (1H), 6.55 (1H), 6.6-6.7 (2H), 6.8 (1H), 7.0 (1H), 7.3 (2H), 7.5 (1H), 7.6-7.8 (2H), 8.05 (1H), 8.1 (1H) and 8.2 (1H) ppm.

Example 26

1-(2,4-Dimethoxybenzenesulfonyl)-5-cyano-2-oxo-3-(2-ethoxyphenyl)-2,3-dihydro-1H-indol-3-yl 4-(4-cyanopyridin-2-yl)piperazine-1-carboxylate $^1$H-NMR (CDCl$_3$): δ=1.25 (3H), 3.2 (2H), 3.5 (1H), 3.55 (3H), 3.6-3.9 (9H), 4.05 (1H), 6.4 (1H), 6.55 (22H), 6.7 (1H), 7.0 (1H), 7.6 (2H), 7.65 (3H), 8.05 (1H), 8.1 (1H) and 8.4 (1H) ppm.

Example 27

1-(2,4-Dimethoxybenzenesulfonyl)-5-cyano-2-oxo-3-(2-ethoxyphenyl)-2,3-dihydro-1H-indol-3-yl 4-(pyrimidin-2-yl)piperazin-1-carboxylate $^1$H-NMR (CDCl$_3$): δ=1.2 (3H), 3.15 (2H), 3.5-3.9 (13H), 4.05 (1H), 6.4 (1H), 6.5 (2H), 6.8 (1H), 7.0 (1H), 7.3 (2H), 7.6-7.7 (2H), 8.05 (2H), 8.1 (1H) and 8.3 (2H) ppm.

Example 28

1-(2,4-Dimethoxybenzenesulfonyl)-5-cyano-2-oxo-3-(2-ethoxyphenyl)-2,3-dihydro-1H-indol-3-yl 4-(4,6-dimethylpyrimidin-2-yl)piperazine-1-carboxylate $^1$H-NMR (CDCl$_3$): δ=1.2 (3H), 2.5 (6H), 3.2 (2H), 3.5 (3H), 3.55-3.9 (10H), 4.05 (1H), 6.3 (1H), 6.4 (1H), 6.55 (1H), 6.8 (1H), 7.0 (1H), 7.3 (1H), 7.6 (1H), 7.65 (1H), 8.05 (1H) and 8.1 (1H) ppm.

Example 29

1-(2,4-Dimethoxybenzenesulfonyl)-5-cyano-2-oxo-3-(2-ethoxyphenyl)-2,3-dihydro-1H-indol-3-yl 4-(pyrazin-2-yl)piperazin-1-carboxylate $^1$H-NMR (CDCl$_3$): δ=1.2 (3H), 3.2-3.9 (15H), 4.05 (1H), 6.4 (1H), 6.55 (1H), 6.8 (1H), 7.0 (1H), 7.5-7.65 (2H), 7.7 (2H), 7.9 (1H) and 8.05-8.2 (4H) ppm.

Example 30

1-(2,4-Dimethoxybenzenesulfonyl)-5-cyano-2-oxo-3-(2-ethoxyphenyl)-2,3-dihydro-1H-indol-3-yl 4-(thiazol-2-yl)piperazine-1-carboxylate $^1$H-NMR (CDCl$_3$): δ=1.2 (3H), 3.25 (2H), 3.4-3.6 (5H), 3.7 (2H), 3.8 (1H), 3.85 (3H), 4.05 (1H), 6.4 (1H), 6.55 (1H), 6.65 (1H), 6.8 (1H), 7.05 (1H), 7.2 (1H), 7.25-7.4 (2H), 7.65 (2H), 8.05 (1H) and 8.15 (4H) ppm.

Example 31

4-(Thiazol-2-yl)piperazine-1-[1-(2,4-dimethoxybenzenesulfonyl)-5-cyano-2-oxo-3-(2-ethoxyphenyl)-2,3-dihydro-1H-indol-3-yl]carboxamide $^1$H-NMR (CDCl$_3$): δ=1.5 (3H), 3.3-3.45 (8H), 3.5 (3H), 3.8 (1H), 4.1-4.35 (2H), 6.4 (1H), 6.55 (1H), 6.6 (1H), 6.85 (1H), 6.9 (1H), 6.95 (1H), 7.2 (1H), 7.3 (1H), 7.6 (2H) and 8.1 (2H) ppm.

Example 32

4-(3-Methylpyridin-2-yl)piperazine-1-[1-(2,4-dimethoxybenzenesulfonyl)-5-cyano-2-oxo-3-(2-ethoxyphenyl)-2,3-dihydro-1H-indol-3-yl]carboxamide $^1$H-NMR (CDCl$_3$): δ=1.5 (3H), 2.25 (3H), 3.1 (4H), 3.35 (4H), 3.5 (3H), 3.85 (3H), 4.1-4.3 (2H), 6.4 (1H), 6.55 (1H), 6.8 (1H), 6.85 (1H), 6.9 (1H), 7.0 (1H), 7.3 (1H), 7.4 (1H), 7.6 (1H), 7.65 (1H), 8.1 (2H) and 8.15 (1H) ppm.

Example 33

4-(5-Cyanopyridin-2-yl)piperazine-1-[1-(2,4-dimethoxybenzenesulfonyl)-5-cyano-2-oxo-3-(2-ethoxyphenyl)-2,3-dihydro-1H-indol-3-yl]carboxamide $^1$H-NMR (CDCl$_3$): δ=1.5 (3H), 3.4 (4H), 3.5 (3H), 3.7 (4H), 3.85 (3H), 4.1-4.3 (2H), 6.4 (1H), 6.65 (2H), 6.8-7.0 (4H), 7.3 (1H), 7.5-7.7 (3H), 8.1 (2H) and 8.4 (1H) ppm.

Example 34

4-(Pyrimidin-2-yl)piperazine-1-[1-(2,4-dimethoxybenzenesulfonyl)-5-cyano-2-oxo-3-(2-ethoxyphenyl)-2,3-dihydro-1H-indol-3-yl]carboxamide $^1$H-NMR (CDCl$_3$): δ=1.5 (3H), 3.3 (4H), 3.5 (3H), 3.7 (4H), 3.85 (3H), 4.1-4.3 (2H), 6.4 (1H), 6.5-6.6 (2H), 6.8 (1H), 6.9 (1H), 6.95 (2H), 7.3 (1H), 7.6 (2H), 8.1 (2H) and 8.3 (2H) ppm.

Example 35

4-(Pyrazin-2-yl)piperazine-1-[1-(2,4-dimethoxybenzenesulfonyl)-5-cyano-2-oxo-3-(2-ethoxyphenyl)-2,3-dihydro-1H-indol-3-yl]carboxamide $^1$H-NMR (CDCl$_3$): δ=1.55 (3H), 3.4 (4H), 3.5 (3H), 3.6 (4H), 3.85 (3H), 4.1-4.3 (2H), 6.4 (1H), 6.55 (1H), 6.85 (1H), 6.9 (1H), 6.95 (2H), 7.3 (1H), 7.6 (2H), 7.9 (1H) and 8.0-8.1 (4H) ppm.

Example 36

4-(Pyridin-4-yl)piperazine-1-[1-(2,4-dimethoxybenzenesulfonyl)-5-cyano-2-oxo-3-(2-ethoxyphenyl)-2,3-dihydro-1H-indol-3-yl]carboxamide $^1$H-NMR (CDCl$_3$): δ=1.5 (3H), 3.35 (4H), 3.4-3.6 (8H), 3.85 (3H), 4.1-4.3 (2H), 6.4 (1H), 6.5 (1H), 6.65 (1H), 6.8 (1H), 6.85 (1H), 6.9 (1H), 7.25 (1H), 7.45 (1H), 7.6 (1H), 7.65 (1H), 8.1 (2H) and 8.2 (1H) ppm.

Example 37

1-(2-Fluorobenzenesulfonyl)-5-cyano-2-oxo-3-(2-ethoxyphenyl)-2,3-dihydro-1H-indol-3-yl 4-(5-cyanopyridin-2-yl)piperazine-1-carboxylate $^1$H-NMR (CDCl$_3$): δ=1.25 (3H), 3.1 (1H), 3.2 (1H), 3.45 (1H), 3.6 (1H), 3.75 (4H), 3.8 (1H), 4.05 (1H), 6.55 (1H), 6.8 (1H), 7.05 (1H), 7.2 (1H), 7.25-7.4 (2H), 7.6-7.75 (4H), 8.15 (2H) and 8.45 (1H) ppm.

Example 38

1-(2,4-Difluorobenzenesulfonyl)-5-cyano-2-oxo-3-(2-ethoxyphenyl)-2,3-dihydro-1H-indol-3-yl 4-(5-cyanopyridin-2-yl)piperazine-1-carboxylate $^1$H-NMR (CDCl$_3$): δ=1.25 (3H), 3.15 (1H), 3.25 (1H), 3.55 (2H), 3.75 (4H), 3.8 (1H), 4.05 (1H), 6.55 (1H), 6.8 (1H), 6.9 (1H), 7.0 (2H), 7.25 (1H), 7.35 (1H), 7.6-7.75 (3H), 8.15 (2H) and 8.4 (1H) ppm.

Example 39

1-(2-Fluorobenzenesulfonyl)-5-cyano-2-oxo-3-(2-ethoxyphenyl)-2,3-dihydro-1H-indol-3-yl 4-(thiazol-2-yl)piperazine-1-carboxylate ¹H-NMR (CDCl₃): δ=1.25 (3H), 3.0-3.3 (3H), 3.4 (1H), 3.55 (2H), 3.7 (2H), 3.8 (1H), 4.05 (1H), 6.6 (1H), 6.8 (1H), 7.05 (1H), 7.2 (2H), 7.25-7.4 (3H), 7.6 (1H), 7.7 (2H) and 8.15 (1H) ppm.

Example 40

1-(2,4-Difluorobenzenesulfonyl)-5-cyano-2-oxo-3-(2-ethoxyphenyl)-2,3-dihydro-1H-indol-3-yl 4-(thiazol-2-yl)piperazine-1-carboxylate ¹H-NMR (CDCl₃): δ=1.25 (3H), 3.1-3.5 (4H), 3.55 (2H), 3.7 (2H), 3.8 (1H), 4.05 (1H), 6.6 (1H), 6.8 (1H), 6.9 (1H), 6.95-7.1 (2H), 7.2 (1H), 7.25 (1H), 7.3 (1H), 7.7 (2H) and 8.1-8.25 (2H) ppm.

Example 41

1-(4-Chlorobenzenesulfonyl)-5-cyano-2-oxo-3-(2-ethoxyphenyl)-2,3-dihydro-1H-indol-3-yl 4-(thiazol-2-yl)piperazine-1-carboxylate ¹H-NMR (CDCl₃): δ=1.25 (3H), 3.25 (2H), 3.3 (1H), 3.4 (1H), 3.55 (2H), 3.65-3.9 (3H), 4.0 (1H), 6.6 (1H), 6.8 (1H), 7.05 (1H), 7.2 (1H), 7.25 (1H), 7.3 (1H), 7.45 (2H), 7.65 (2H), 8.05 (2H) and 8.1 (1H) ppm.

Example 42

1-(4-Cyanobenzenesulfonyl)-5-cyano-2-oxo-3-(2-ethoxyphenyl)-2,3-dihydro-1H-indol-3-yl 4-(thiazol-2-yl)piperazine-1-carboxylate ¹H-NMR (CDCl₃): δ=1.25 (3H), 3.0-3.2 (2H), 3.35 (2H), 3.55 (2H), 3.7 (2H), 3.8 (1H), 4.05 (1H), 6.65 (1H), 6.8 (1H), 7.1 (1H), 7.20 (1H), 7.25-7.4 (2H), 7.7 (2H), 7.8 (2H), 8.15 (1H) and 8.2 (2H) ppm.

Example 43

4-(5-Cyanopyridin-2-yl)piperazine-1-[1-(4-nitrobenzenesulfonyl)-5-cyano-2-oxo-3-(2-ethoxyphenyl)-2,3-dihydro-1H-indol-3-yl]carboxamide ¹H-NMR (CDCl₃): δ=1.5 (3H), 3.2-3.4 (4H), 3.55-3.8 (4H), 4.15 (1H), 4.25 (1H), 6.5 (1H), 6.55 (1H), 6.95 (2H), 7.15 (1H), 7.3 (1H), 7.45 (1H), 7.65 (2H), 8.05 (1H), 8.3 (4H) and 8.4 (1H) ppm.

Example 44

4-(5-Cyanopyridin-2-yl)piperazine-1-[1-(2,4-difluorobenzenesulfonyl)-5-cyano-2-oxo-3-(2-ethoxyphenyl)-2,3-dihydro-1H-indol-3-yl]carboxamide ¹H-NMR (CDCl₃): δ=1.5 (3H), 3.2-3.45 (4H), 3.55-3.8 (4H), 4.15 (1H), 4.2 (1H), 6.55 (1H), 6.6 (1H), 6.85-7.05 (4H), 7.1 (1H), 7.3 (1H), 7.55 (1H), 7.65 (2H), 8.1 (1H), 8.2 (1H) and 8.4 (1H) ppm.

Example 45

4-(5-Cyanopyridin-2-yl)piperazine-1-[1-(2-methoxybenzenesulfonyl)-5-cyano-2-oxo-3-(2-ethoxyphenyl)-2,3-dihydro-1H-indol-3-yl]carboxamide ¹H-NMR (CDCl₃): δ=1.55 (3H), 3.4 (4H), 3.55 (3H), 3.6-3.75 (4H), 4.2 (1H), 4.25 (1H), 6.55 (1H), 6.75-7.0 (5H), 7.1 (1H), 7.3 (1H), 7.55 (1H), 7.6 (3H), 8.1 (1H), 8.15 (1H) and 8.4 (1H) ppm.

Example 46

4-(5-Cyanopyridin-2-yl)piperazine-1-[1-(4-chlorobenzenesulfonyl)-5-cyano-2-oxo-3-(2-ethoxyphenyl)-2,3-dihydro-1H-indol-3-yl]carboxamide ¹H-NMR (CDCl₃): δ=1.5 (3H), 3.2-3.4 (4H), 3.6-3.8 (4H), 4.1 (1H), 4.2 (1H), 6.5 (1H), 6.55 (1H), 6.95 (2H), 7.1 (1H), 7.3 (1H), 7.45 (3H), 7.65 (2H), 8.05 (3H) and 8.4 (1H) ppm.

Example 47

4-(5-Cyanopyridin-2-yl)piperazine-1-[1-(4-cyanobenzenesulfonyl)-5-cyano-2-oxo-3-(2-ethoxyphenyl)-2,3-dihydro-1H-indol-3-yl]carboxamide ¹H-NMR (CDCl₃): δ=1.5 (3H), 3.2-3.4 (4H), 3.55-3.8 (4H), 4.15 (1H), 4.2 (1H), 6.5 (1H), 6.55 (1H), 6.9-7.0 (2H), 7.1 (1H), 7.35 (1H), 7.5 (1H), 7.65 (2H), 7.8 (2H), 8.05 (1H), 8.2 (2H) and 8.4 (1H) ppm.

Example 48

4-(5-Cyanopyridin-2-yl)piperazine-1-[1-benzenesulfonyl-5-cyano-2-oxo-3-(2-ethoxyphenyl)-2,3-dihydro-1H-indol-3-yl]carboxamide ¹H-NMR (CDCl₃): δ=1.5 (3H), 3.25-3.4 (4H), 3.55-3.8 (4H), 4.15 (1H), 4.2 (1H), 6.55 (1H), 6.6 (1H), 6.85-7.0 (2H), 7.0 (1H), 7.3 (1H), 7.55 (3H), 7.65 (3H), 8.05 (1H), 8.15 (2H) and 8.4 (1H) ppm.

Example 49

4-(5-Cyanopyridin-2-yl)piperazin-1-[1-(2-fluorobenzenesulfonyl)-5-cyano-2-oxo-3-(2-ethoxyphenyl)-2,3-dihydro-1H-indol-3-yl]carboxamide ¹H-NMR (CDCl₃): δ=1.5 (3H), 3.2-3.45 (4H), 3.55-3.8 (4H), 4.15 (1H), 4.2 (1H), 6.6 (2H), 6.95 (2H), 7.1 (1H), 7.2 (2H), 7.3 (1H), 7.5 (1H), 7.65 (2H), 8.05 (1H), 8.15 (2H) and 8.4 (1H) ppm.

Example 50

4-(5-Cyanopyridin-2-yl)piperazine-1-[1-(4-cyanobenzenesulfonyl)-5-cyano-2-oxo-3-(2-ethoxyphenyl)-2,3-dihydro-1H-indol-3-yl]carboxamide ¹H-NMR (CDCl₃): δ=1.25 (3H), 3.1 (2H), 3.5 (2H), 3.7 (2H), 3.75-3.9 (3H), 4.05 (1H), 6.6 (1H), 6.8 (1H), 7.05 (1H), 7.25 (1H), 7.35 (1H), 7.6-7.75 (3H), 7.8 (2H), 8.1 (1H), 8.2 (2H) and 8.4 (1H) ppm.

We claim:

1. A compound of the formula (I)

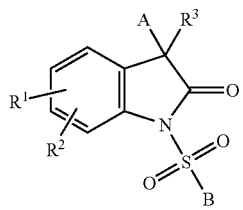

in which

A is phenyl or naphthalene, each of which can be substituted by one, two, three or four radicals $R^4$ which are selected independently of one another from the group consisting of hydrogen, chlorine, bromine, iodine, fluorine, $(CH_2)_{0-2}$—CN, $CF_3$, $OCF_3$, $CONH_2$, $CONH(C_1\text{-}C_4\text{-alkyl})$, $CON(C_1\text{-}C_4\text{-alkyl})(C_1\text{-}C_4\text{-alkyl})$, NHCHO, $NHCONH_2$, $NH(C_0\text{-}C_4\text{-alkylene})CONH_2$, $NH(C_0\text{-}C_4\text{-alkylene})CONH(C_1\text{-}C_4\text{-alkyl})$, $NHCOCH_3$, $NO_2$, $(CH_2)_{0-2}$—OH, O—$C_1\text{-}C_6\text{-alkyl}$, $(CH_2)_{1-2}$—O—$C_1\text{-}C_4\text{-alkyl}$, O—$C_0\text{-}C_4\text{-alkylene-phenyl}$, phenyl, $C_1\text{-}C_6$-alkyl, $C_2\text{-}C_6$-alkenyl and $C_2\text{-}C_6$-alkynyl, B is an aromatic or partially aromatic monocyclic or bicyclic system which may be composed of 6, 7, 8, 9 or 10 C atom members and which may be substituted by one, two, three or four radicals selected from the group consisting of the radicals $R^6$, $R^7$, $R^8$ and $R^9$, where $R^6$, $R^7$, $R^8$ and $R^9$ are selected, independently of one another and independently of their respective occurrence, from the group consisting of hydrogen, chlorine, bromine, iodine, fluorine, $(CH_2)_{0-2}$—CN, $CF_3$, $OCF_3$, $CONH_2$, $CONH(C_1\text{-}C_4\text{-alkyl})$, $CON(C_1\text{-}C_4\text{-alkyl})(C_1\text{-}C_4\text{-alkyl})$, NHCHO, $NH(C_{0-4}\text{-alkylene})CONH(C_1\text{-}C_4\text{-alkyl})$, $NHCOCH_3$, $NO_2$, OH, O—$C_1\text{-}C_4\text{-alkyl}$, $(CH_2)_{0-2}$—O—$(CH_2)_{0-3}$—$CH_3$, O—$C_0\text{-}C_4\text{-alkylene-phenyl}$, phenyl, $C_1\text{-}C_6$-alkyl, $C_2\text{-}C_6$-alkenyl and $C_2\text{-}C_6$-alkynyl;

$R^1$ is CN;

$R^2$ is hydrogen;

$R^3$ is a radical (W)—(X)—(Y)—Z, where

W is $C_1\text{-}C_4$-alkylene, $(C_0\text{-}C_4\text{-alkylene})$-O—$(C_0\text{-}C_4\text{-alkylene})$ or $(C_0\text{-}C_4\text{-alkylene})$-$NR^5$—$(C_0\text{-}C_4\text{-alkylene})$, in which $R^5$ is hydrogen or $C_1\text{-}C_4$-alkyl, X is CO, $SO_2$, (C=NH) or (C=N—CN);

Y is a radical selected from the group consisting of the radicals

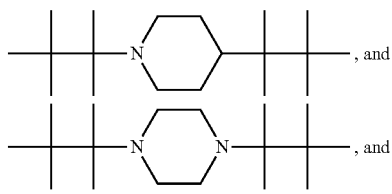

Z is a radical selected from the group consisting of the radicals

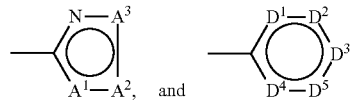

where $A^2$ and $A^3$ independently of one another are N or C;

$A^1$ is N, C, O or S;

$D^1$, $D^2$, $D^3$, $D^4$ and $D^5$ independently of one another are C or N, but where at least one of the variables $D^1$, $D^2$, $D^3$, $D^4$ and $D^5$ is N, and where Z may in each case be substituted by the radicals $R^{12}$, $R^{13}$ and $R^{14}$, where $R^{12}$, $R^{13}$ and $R^{14}$ have independently of one another the meanings mentioned below, namely $R^{12}$ is hydrogen, chlorine, fluorine CN, $CF_3$, $OCF_3$, $CONH_2$, $NHCOCH_3$, $NO_2$, OH, O—$C_1\text{-}C_4$-alkyl, $C_1\text{-}C_4$-alkyl, $NH_2$, $NH(C_1\text{-}C_4\text{-alkyl})$ or $N(C_1\text{-}C_4\text{-alkyl})(C_1\text{-}C_4\text{-alkyl})$;

$R^{13}$ is hydrogen, chlorine, fluorine, OCH, or $C_1\text{-}C_4$-alkyl;

$R^{14}$ is hydrogen;

or a tautomeric, enantiomeric or diastereomeric form, or a physiologically tolerated salt of said compound.

2. The compound of formula (I) according to claim 1, in which $R^1$, $R^2$ and $R^3$ have the meanings stated in claim 1 and

A is a phenyl ring which may be substituted by one or two radicals $R^4$, where $R^4$ independently of one another have the meanings stated in claim 1;

B is a phenyl ring which may be substituted by one, two, three or four radicals selected from the group consisting of the radicals $R^6$, $R^7$, $R^8$ and $R^9$, where $R^6$, $R^7$, $R^8$ and $R^9$ independently of one another and independently of their respective occurrence have the meanings stated in claim 1;

or a tautomeric, enantiomeric or diastereomeric form, or a physiologically tolerated salt of said compound.

3. The compound of formula (I) according to claim 1, in which

A is a phenyl ring which may be substituted by one or two radicals $R^4$ which are selected independently of one another from the group consisting of hydrogen, chlorine, O—$C_1\text{-}C_4$-alkyl, $(CH_2)_{1-2}$—O—$(CH_2)_{0-2}$—CH, and $C_1\text{-}C_6$-alkyl, B is a phenyl ring which may be substituted by one, two, three or four radicals selected from the group consisting of the radicals $R^6$, $R^7$, $R^8$ and $R^9$, where $R^6$, $R^7$, $R^8$ and $R^9$ are selected independently of one another and independently of their respective occurrence from the group consisting of hydrogen, fluorine, chlorine, CN, $NO_2$, O—$C_1\text{-}C_4$-alkyl, $(CH_2)_{1-2}$—O—$(CH_2)_{0-2}$—CH, and $C_1\text{-}C_6$-alkyl, $R^1$ is CN and is located in position 5 of the oxindole of the formula (I), $R^2$ is hydrogen, $R^3$ is a radical (W)—(X)—(Y)—Z, where W is O, $CH_2NH$, $NHCH_2$, $OCH_2$, $CH_2O$ or NH, X is CO, (C=NH) or (C=N—CN), Y is a radical selected from the group consisting of the radicals

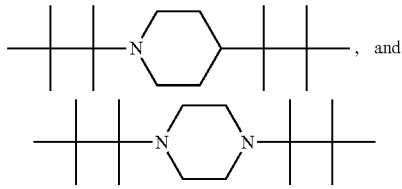

Z is a radical selected from the group consisting of the radicals

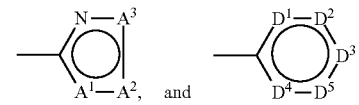

where $A^2$ and $A^3$ independently of one another are N or C;

$A^1$ is N, C, O or S;

$D^1$, $D^2$, $D^3$, $D^4$ and $D^5$ independently of one another are C or N, but where at least one of the variables $D^1$, $D^2$, $D^3$, $D^4$ or $D^5$ is N, and where Z may in each case additionally be substituted by the radicals $R^{12}$, $R^{13}$ and $R^{14}$, where $R^{12}$, $R^{13}$ and $R^{14}$ independently of one another have the meanings stated below, namely $R^{12}$ is hydrogen, chlorine, fluorine, CN, $CF_3$, $OCF_3$, $CONH_2$, $NHCOCH_3$, $NO_2$, OH, O—$C_1$-$C_4$-alkyl, $C_1$-$C_4$-alkyl, $NH_2$, NH($C_1$-$C_4$-alkyl) or N($C_1$-$C_4$-alkyl)($C_1$-$C_4$-alkyl);

$R^{13}$ is hydrogen, chlorine, fluorine, $OCH_3$ or $C_1$-$C_4$-alkyl;

$R^{14}$ is hydrogen;

or a tautomeric, enantiomeric or diastereomeric form, or a physiologically tolerated salt of said compound.

4. The compound of formula (I) according to claim 1, in which

A is a phenyl ring which may be substituted by one radical $R^4$, where $R^4$ is chlorine, O—$C_1$-$C_4$-alkyl, or $C_1$-$C_6$-alkyl;

B is a phenyl ring which may be substituted by one or two radicals selected from the group consisting of the radicals $R^6$ and $R^7$, where $R^6$ and $R^7$ are independently of one another and independently of their respective occurrence selected from the group consisting of hydrogen, fluorine, chlorine, CN, $NO_2$, O—$C_1$-$C_4$-alkyl and $C_1$-$C_6$-alkyl;

$R^1$ is CN and is located in position 5 of the oxindole of the formula (I);

$R^2$ is hydrogen;

$R^3$ is a radical (W)—(X)—(Y)—Z, where

W is O, $CH_2$ or NH,

X is CO, (C=NH) or (C=N—CN),

Y is a radical selected from the group consisting of the radicals

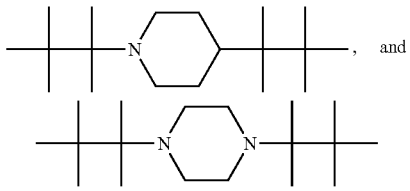

Z is a radical selected from the group consisting of the radicals

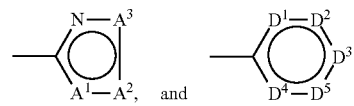

where $A^2$ and $A^3$ independently of one another are N or C;

$A^1$ is N, C, O or S;

$D^1$, $D^2$, $D^3$, $D^4$ and $D^5$ independently of one another are C or N, but where at least one of the variables $D^1$, $D^2$, $D^3$, $D^4$ and $D^5$ is N, and where Z may in each case be substituted by the radicals $R^{12}$, $R^{13}$ and $R^{14}$, where $R^{12}$, $R^{13}$ and $R^{14}$ independently of one another have the meanings stated below, namely $R^{12}$ is hydrogen, chlorine, fluorine, CN, $CF_3$, $OCF_3$, $CONH_2$, $NHCOCH_3$, $NO_2$, OH, O—$C_1$-$C_4$-alkyl, $C_1$-$C_4$-alkyl, $NH_2$, NH($C_1$-$C_4$-alkyl) or N($C_1$-$C_4$-alkyl)($C_1$-$C_4$-alkyl);

$R^{13}$ is hydrogen, fluorine, chlorine, $OCH_3$ or $C_1$-$C_4$-alkyl;

$R^{14}$ is hydrogen;

or a tautomeric, enantiomeric or diastereomeric form, or a physiologically tolerated salt of said compound.

5. The compound of formula (I) according to claim 1, in which

A is a phenyl ring which may be substituted by $R^4$, where $R^4$ is chlorine, $OCH_2CH_3$, $OCH(CH_3)_2$, $OCH_2CH_2CH_3$, $CH_2CH_3$, $CH(CH_3)_2$, or $CH_2CH_2CH_3$, B is a phenyl ring which may be substituted by one or two radicals selected from the group consisting of the radicals $R^6$ and $R^7$, where $R^6$ and $R^7$ are independently of one another and independently of their respective occurrence selected from the group consisting of hydrogen, fluorine, chlorine, CN, $NO_2$, O—$C_1$-$C_4$-alkyl, and $C_1$-$C_6$-alkyl;

$R^1$ is CN and is located in position 5 of the oxindole of the formula (I);

$R^2$ is hydrogen;

$R^3$ is a radical (W)—(X)—(Y)—Z, where

W is $CH_2$, O or NH,

X is CO or (C=NH),

Y is the radical

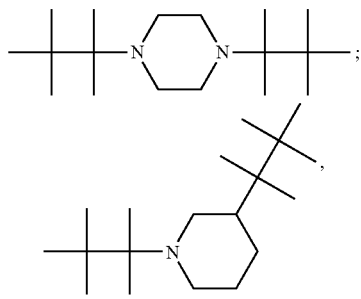

Z is a radical selected from the group consisting of the radicals pyridyl, pyrimidinyl, pyrazinyl, thiazolyl, isoxazolyl, imidazolyl and phthalazinyl
and where
Z in each case is substituted by $R^{12}$ and $R^{13}$, where $R^{12}$ and $R^{13}$ independently of one another have the meanings stated below, namely
$R^{12}$ is hydrogen, chlorine, fluorine, CN, $CF_3$, $OCF_3$, OH, $OC_1$-$C_4$-alkyl, $C_1$-$C_4$-alkyl, $NH_2$, $NH(C_1$-$C_4$-alkyl) or $N(C_1$-$C_4$-alkyl)($C_1$-$C_4$-alkyl);
$R^{13}$ is hydrogen, fluorine or $C_1$-$C_4$-alkyl;
or a tautomeric, enantiomeric or diastereomeric form, or a physiologically tolerated salt of said compound.

6. The compound of formula (I) according to claim 1, in which
A is a phenyl ring which is substituted by O—$CH_2CH_3$ in the ortho position,
B is a phenyl ring which is substituted by one or two radicals selected from the group consisting of the radicals $R^6$ and $R^7$, where $R^6$ and $R^7$ are selected independently of one another and independently of their respective occurrence from the group consisting of hydrogen, fluorine, chlorine, CN, $NO_2$, O—$C_1$-$C_4$-alkyl, and $C_1$-$C_6$-alkyl,
$R^1$ is CN and is located in position 5 of the oxindole of the formula (I),
$R^2$ is hydrogen,
$R^3$ is a radical (W)—(X)—(Y)—Z, where
W is $CH_2$, O or NH,
X is CO or (C=NH),
Y is a radical

Z is a radical selected from the group consisting of the radicals

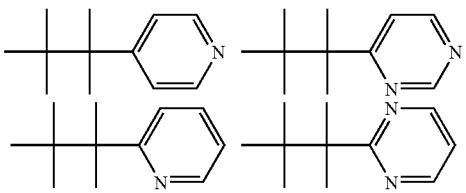

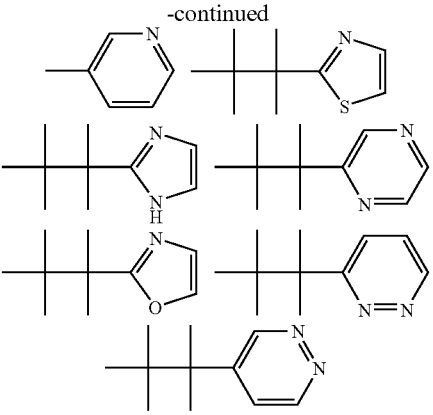

and where Z may in each case be substituted by the radicals $R^{12}$ and $R^{13}$, where $R^{12}$ and $R^{13}$ independently of one another have the meanings stated below, namely
$R^{12}$ is hydrogen, chlorine, fluorine, CN, $CF_3$, $OCF_3$, OH, $OCH_3$, $CH_3$, $CH_2CH_3$, $CH(CH_3)_2$, $NH_2$, $NHCH_3$ or $N(CH_3)_2$;
$R^{13}$ is hydrogen, chlorine, fluorine or $CH_3$, $CH_2CH_3$;
or a tautomeric, enantiomeric or diastereomeric, or a physiologically tolerated salt of said compound.

7. The compound according to claim 1, having a binding affinity Ki for the vasopressin V1b receptor subtype of less than about 100 nM.

8. The compound of formula (I) according to claim 1, selected from the group consisting of:
5-Cyano-1-(2,4-dimethoxybenzenesulfonyl)-3-(2-ethoxyphenyl)-2-oxo-2,3-dihydro-1H-indol-3-yl 4-(6-methylpyridin-2-yl)piperazine-1-carboxylate;
5-Cyano-1-(2-methoxybenzenesulfonyl)-3-(2-ethoxyphenyl)-2-oxo-2,3-dihydro-1H-indol-3-yl 4-(pyridin-4-yl)piperazine-1-carboxylate;
5-Cyano-1-(2,4-dimethoxybenzenesulfonyl)-3-(2-ethoxyphenyl)-2-oxo-2,3-dihydro-1H-indol-3-yl 4-(pyridin-4-yl)piperazine-1-carboxylate;
5-Cyano-1-(2-methoxybenzenesulfonyl)-3-(2-ethoxyphenyl)-2-oxo-2,3-dihydro-1H-indol-3-yl 4-(thiazol-2-yl)piperazine-1-carboxylate;
5-Cyano-1-(2-methoxybenzenesulfonyl)-3-(2-ethoxyphenyl)-2-oxo-2,3-dihydro-1H-indol-3-yl 4-(5-cyanopyridin-2-yl)piperazine-1-carboxylate;
5-Cyano-1-(4-chlorobenzenesulfonyl)-3-(2-ethoxyphenyl)-2-oxo-2,3-dihydro-1H-indol-3-yl 4-(5-cyanopyridin-2-yl)piperazine-1-carboxylate;
5-Cyano-1-(2,4-difluorobenzenesulfonyl)-3-(2-ethoxyphenyl)-2-oxo-2,3-dihydro-1H-indol-3-yl 4-(pyridin-4-yl) piperazine-1-carboxylate;
5-Cyano-1-(2-fluorobenzenesulfonyl)-3-(2-ethoxyphenyl)-2-oxo-2,3-dihydro-1H-indol-3-yl 4-(pyridin-4-yl)piperazine-1-carboxylate;
5-Cyano-1-benzenesulfonyl-3-(2-ethoxyphenyl)-2-oxo-2,3-dihydro-1H-indol-3-yl 4-(pyridin-4-yl)-piperazine-1-carboxylate;
4-(Pyridin-4-yl)piperazine-1-[1-(2-methoxybenzenesulfonyl)-5-cyano-2-oxo-3-(2-ethoxyphenyl)-2,3-dihydro-1H-indol-3-yl]carboxamide;
4-(Pyridin-4-yl)piperazine-1-[1-benzenesulfonyl-5-cyano-2-oxo-3-(2-ethoxyphenyl)-2,3-dihydro-1H-indol-3-yl]carboxamide;

4-(Pyridin-4-yl)piperazine-1-[1-(2-fluorobenzenesulfonyl)-5-cyano-2-oxo-3-(2-ethoxyphenyl)-2,3-dihydro-1H-indol-3-yl]carboxamide;

4-(Pyridin-4-yl)piperazine-1-[1-(2,4-difluorobenzenesulfonyl)-5-cyano-2-oxo-3-(2-ethoxyphenyl)-2,3-dihydro-1H-indol-3-yl]carboxamide;

4-(Pyridin-4-yl)piperazine-1-[1-(4-cyanobenzenesulfonyl)-5-cyano-2-oxo-3-(2-ethoxyphenyl)-2,3-dihydro-1H-indol-3-yl]carboxamide;

4-(Pyridin-4-yl)piperazine-1-[1-(2-methoxy-4-methylbenzenesulfonyl)-5-cyano-2-oxo-3-(2-ethoxyphenyl)-2,3-dihydro-1H-indol-3-yl]carboxamide;

4-(Pyridin-4-yl)piperazine-1-[1-(2,4-dimethoxybenzenesulfonyl)-5-cyano-2-oxo-3-(2-ethoxyphenyl)-2,3-dihydro-1H-indol-3-yl]carboxamide;

4-(Pyridin-4-yl)piperazine-1-[1-(4-nitrobenzenesulfonyl)-5-cyano-2-oxo-3-(2-ethoxyphenyl)-2,3-dihydro-1H-indol-3-yl]carboxamide;

1-(4-Cyanobenzenesulfonyl)-5-cyano-2-oxo-3-(2-ethoxyphenyl)-2,3-dihydro-1H-indol-3-yl 4-(pyridin-4-yl)piperazine-1-carboxylate;

1-(4-Nitrobenzenesulfonyl)-5-cyano-2-oxo-3-(2-ethoxyphenyl)-2,3-dihydro-1H-indol-3-yl 4-(pyridin-4-yl)piperazine-1-carboxylate;

[1-(2-Methoxy-4-methylbenzenesulfonyl)-5-cyano-2-oxo-3-(2-ethoxyphenyl)-2,3-dihydro-1H-indol-3-yl 4-(pyridin-4-yl)piperazine-1-carboxylate;

1-(4-Fluorobenzenesulfonyl)-5-cyano-2-oxo-3-(2-ethoxyphenyl)-2,3-dihydro-1H-indol-3-yl 4-(pyridin-4-yl)piperazine-1-carboxylate;

1-(2,4-Dimethoxybenzenesulfonyl)-5-cyano-2-oxo-3-(2-ethoxyphenyl)-2,3-dihydro-1H-indol-3-yl 4-(3-cyanopyridin-2-yl) piperazine-1-carboxylate;

1-(2,4-Dimethoxybenzenesulfonyl)-5-cyano-2-oxo-3-(2-ethoxyphenyl)-2,3-dihydro-1H-indol-3-yl 4-(3-methylpyridin-2-yl) piperazine-1-carboxylate;

1-(2,4-Dimethoxybenzenesulfonyl)-5-cyano-2-oxo-3-(2-ethoxyphenyl)-2,3-dihydro-1H-indol-3-yl 4-(4-methylpyridin-2-yl) piperazine-1-carboxylate;

1-(2,4-Dimethoxybenzenesulfonyl)-5-cyano-2-oxo-3-(2-ethoxyphenyl)-2,3-dihydro-1H-indol-3-yl 4-(pyridin-2-yl) piperazine-1-carboxylate;

1-(2,4-Dimethoxybenzenesulfonyl)-5-cyano-2-oxo-3-(2-ethoxyphenyl)-2,3-dihydro-1H-indol-3-yl 4-(4-cyanopyridin-2-yl) piperazine-1-carboxylate;

1-(2,4-Dimethoxybenzenesulfonyl)-5-cyano-2-oxo-3-(2-ethoxyphenyl)-2,3-dihydro-1H-indol-3-yl 4-(pyrimidin-2-yl) piperazin-1-carboxylate;

1-(2,4-Dimethoxybenzenesulfonyl)-5-cyano-2-oxo-3-(2-ethoxyphenyl)-2,3-dihydro-1H-indol-3-yl 4-(4,6-dimethylpyrimidin-2-yl)piperazine-1-carboxylate;

1-(2,4-Dimethoxybenzenesulfonyl)-5-cyano-2-oxo-3-(2-ethoxyphenyl)-2,3-dihydro-1H-indol-3-yl 4-(pyrazin-2-yl)piperazine-1-carboxylate;

1-(2,4-Dimethoxybenzenesulfonyl)-5-cyano-2-oxo-3-(2-ethoxyphenyl)-2,3-dihydro-1H-indol-3-yl 4-(thiazol-2-yl) piperazine-1-carboxylate;

4-(Thiazol-2-yl) piperazine-1-[1-(2,4-dimethoxybenzenesulfonyl)-5-cyano-2-oxo-3-(2-ethoxyphenyl)-2,3-dihydro-1H-indol-3-yl]carboxamide;

4-(3-Methylpyridin-2-yl) piperazine-1-[1-(2,4-dimethoxybenzenesulfonyl)-5-cyano-2-oxo-3-(2-ethoxyphenyl)-2,3-dihydro-1H-indol-3-yl]carboxamide;

4-(5-Cyanopyridin-2-yl)piperazine-1-[1-(2,4-dimethoxybenzenesulfonyl)-5-cyano-2-oxo-3-(2-ethoxyphenyl)-2,3-dihydro-1H-indol-3-yl]carboxamide;

4-(Pyrimidin-2-yl)piperazine-1-[1-(2,4-dimethoxybenzenesulfonyl)-5-cyano-2-oxo-3-(2-ethoxyphenyl)-2,3-dihydro-1H-indol-3-yl]carboxamide;

4-(Pyrazin-2-yl) piperazine-1-[1-(2,4-dimethoxybenzenesulfonyl)-5-cyano-2-oxo-3-(2-ethoxyphenyl)-2,3-dihydro-1H-indol-3-yl]carboxamide;

4-(Pyridin-4-yl)piperazine-1-[1-(2,4-dimethoxybenzenesulfonyl)-5-cyano-2-oxo-3-(2-ethoxyphenyl)-2,3-dihydro-1H-indol-3-yl]carboxamide;

1-(2-Fluorobenzenesulfonyl)-5-cyano-2-oxo-3-(2-ethoxyphenyl)-2,3-dihydro-1H-indol-3-yl 4-(5-cyanopyridin-2-yl)piperazine-1-carboxylate;

1-(2,4-Difluorobenzenesulfonyl)-5-cyano-2-oxo-3-(2-ethoxyphenyl)-2,3-dihydro-1H-indol-3-yl 4-(5-cyanopyridin-2-yl)piperazine-1-carboxylate;

1-(2-Fluorobenzenesulfonyl)-5-cyano-2-oxo-3-(2-ethoxyphenyl)-2,3-dihydro-1H-indol-3-yl 4-(thiazol-2-yl)piperazine-1-carboxylate;

1-(2,4-Difluorobenzenesulfonyl)-5-cyano-2-oxo-3-(2-ethoxyphenyl)-2,3-dihydro-1H-indol-3-yl 4-(thiazol-2-yl) piperazine-1-carboxylate;

1-(4-Chlorobenzenesulfonyl)-5-cyano-2-oxo-3-(2-ethoxyphenyl)-2,3-dihydro-1H-indol-3-yl 4-(thiazol-2-yl)piperazine-1-carboxylate;

1-(4-Cyanobenzenesulfonyl)-5-cyano-2-oxo-3-(2-ethoxyphenyl)-2,3-dihydro-1H-indol-3-yl 4-(thiazol-2-yl)piperazine-1-carboxylate;

4-(5-Cyanopyridin-2-yl)piperazine-1-[1-(4-nitrobenzenesulfonyl)-5-cyano-2-oxo-3-(2-ethoxyphenyl)-2,3-dihydro-1H-indol-3-yl]carboxamide;

4-(5-Cyanopyridin-2-yl)piperazine-1-[1-(2,4-difluorobenzenesulfonyl)-5-cyano-2-oxo-3-(2-ethoxyphenyl)-2,3-dihydro-1H-indol-3-yl]carboxamide;

4-(5-Cyanopyridin-2-yl)piperazine-1-[1-(2-methoxybenzenesulfonyl)-5-cyano-2-oxo-3-(2-ethoxyphenyl)-2,3-dihydro-1H-indol-3-yl]carboxamide;

4-(5-Cyanopyridin-2-yl)piperazine-1-[1-(4-chlorobenzenesulfonyl)-5-cyano-2-oxo-3-(2-ethoxyphenyl)-2,3-dihydro-1H-indol-3-yl]carboxamide;

4-(5-Cyanopyridin-2-yl)piperazine-1-[1-(4-cyanobenzenesulfonyl)-5-cyano-2-oxo-3-(2-ethoxyphenyl)-2,3-dihydro-1H-indol-3-yl]carboxamide;

4-(5-Cyanopyridin-2-yl)piperazine-1-[1-benzenesulfonyl-5-cyano-2-oxo-3-(2-ethoxyphenyl)-2,3-dihydro-1H-indol-3-yl]carboxamide;

4-(5-Cyanopyridin-2-yl)piperazin-1-[1-(2-fluorobenzenesulfonyl)-5-cyano-2-oxo-3-(2-ethoxyphenyl)-2,3-dihydro-1H-indol-3-yl]carboxamide; and 4-(5-Cyanopyridin-2-yl)piperazine-1-[1-(4-cyanobenzenesulfonyl)-5-cyano-2-oxo-3-(2-ethoxyphenyl)-2,3-dihydro-1H-indol-3-yl]carboxamide.

9. A composition comprising at least one compound of the formula (I) according to claim 1 and a pharmaceutically acceptable carrier.

10. A method for the treatment of arterial hypertension or congestive heart failure (CHF) diseases in a mammal in need of such treatment comprising administering to said mammal an effective amount of at least one compound of the formula (I) according to claim 1.

* * * * *